United States Patent
Kletschka

(12) 
(10) Patent No.: US 6,485,456 B1
(45) Date of Patent: Nov. 26, 2002

(54) EMBOLIC PROTECTION DEVICE HAVING EXPANDABLE TRAP

(76) Inventor: Harold D. Kletschka, 1925 Noble Dr., Minneapolis, MN (US) 55422-4158

(*) Notice: Subject to any disclaimer, the term of this patent is extended or adjusted under 35 U.S.C. 154(b) by 0 days.

(21) Appl. No.: 10/133,031

(22) Filed: Apr. 26, 2002

Related U.S. Application Data

(63) Continuation of application No. 09/495,833, filed on Feb. 1, 2000, now Pat. No. 6,443,926.

(51) Int. Cl.$^7$ .............................................. A61M 29/00
(52) U.S. Cl. ..................... 604/96.01; 604/104; 604/108; 604/109; 606/159; 606/194; 606/200
(58) Field of Search ...................... 604/96.01, 104–109; 606/200, 198, 191, 194, 159

(56) References Cited

U.S. PATENT DOCUMENTS

| | | | |
|---|---|---|---|
| 4,503,569 A | * | 3/1985 | Dotter .......................... 606/200 |
| 4,794,928 A | | 1/1989 | Kletschka |
| 4,909,258 A | | 3/1990 | Kuntz et al. |
| 4,966,596 A | | 10/1990 | Kuntz et al. |
| 5,120,323 A | | 6/1992 | Shockey et al. |
| 5,242,460 A | | 9/1993 | Klein et al. |
| 5,441,516 A | * | 8/1995 | Wang et al. ................. 606/200 |
| 5,662,671 A | | 9/1997 | Barbut et al. ............... 606/170 |
| 5,814,064 A | | 9/1998 | Daniel et al. ............... 606/200 |
| 5,833,644 A | | 11/1998 | Zadno-Azizi et al. |
| 5,833,650 A | | 11/1998 | Imran |
| 5,954,745 A | | 9/1999 | Gertler et al. .............. 606/200 |
| 6,001,118 A | | 12/1999 | Daniel et al. |
| 6,022,336 A | | 2/2000 | Zadno-Azizi et al. |
| 6,050,972 A | | 4/2000 | Zadno-Azizi et al. |
| 6,068,623 A | | 5/2000 | Zadno-Azizi et al. |
| 6,165,200 A | | 12/2000 | Tsugita ....................... 606/200 |
| 6,231,588 B1 | | 5/2001 | Zadno-Azizi et al. ....... 606/200 |
| 6,398,756 B2 | * | 6/2002 | Peterson et al. ......... 604/96.01 |

FOREIGN PATENT DOCUMENTS

| | | |
|---|---|---|
| WO | 9744082 | 11/1997 |
| WO | 9744084 | 11/1997 |
| WO | 9744085 | 11/1997 |

(List continued on next page.)

OTHER PUBLICATIONS

*International Congress XII on Endovascular Interventions*, Henry et al.; A New Cerebral Protection Device for Carotid Angioplasty and Stenting. First Clinical Experience with the PercuSurge Guardwire.

Harold D. Kletschka, M.D.; Projected Enhancement and Extension of Application Transluminal Angioplasty Catheters Using Kletschka Angioplasty Trap–Barrier Device; p. 1–29.

Oesterle et al.; A Coaxial Catheter; System for the Prevention of Distal Embolization.

*Simon Nitinol Filter*.

(List continued on next page.)

Primary Examiner—Gregory Huson
Assistant Examiner—Tuan Nguyen
(74) Attorney, Agent, or Firm—Dorsey & Whitney LLP

(57) ABSTRACT

An embolic protection device for use in medical, veterinary, non-medical or industrial applications where removal of an obstruction from a small diameter vessel or vessel-like structure could produce particles, which, if allowed to remain in the vessel, could cause undesirable complications and results. One embodiment comprises a catheter for insertion into a vessel and a trap operably connected to the catheter and to a rotatable member. Rotating the rotatable member relative to the catheter actuates the trap. One embodiment comprises a rotatable member that actuates a flexible strut between an arcuately expanded position and a helically twisted position, and a membrane operably connected to the flexible strut.

19 Claims, 28 Drawing Sheets

FOREIGN PATENT DOCUMENTS

| | | |
|---|---|---|
| WO | 9838929 | 9/1998 |
| WO | 9838930 | 9/1998 |
| WO | 9839044 | 9/1998 |
| WO | 9856440 | 12/1998 |
| WO | 9926692 | 6/1999 |
| WO | 9942059 | 8/1999 |
| WO | 9942157 | 8/1999 |
| WO | 9942158 | 8/1999 |
| WO | 9942164 | 8/1999 |
| WO | 0007657 | 2/2000 |
| WO | 0029060 | 5/2000 |
| WO | 0050113 | 8/2000 |
| WO | 0054673 | 9/2000 |

OTHER PUBLICATIONS

*Clinical Neurosurgery, Proceedings of the Congress of Neurological Surgeons*, Smith et al.; Transluminal Angioplasty of the Cerebral Circulation; 1983; pp. 117–134.

*Radiology*, Kensy et al.; Recanalization of Obstructed Arteries with a Flexible, Rotating Tip Catheter, Nov. 1987, pp. 387–389.

*Journal of Vascular Surgery*, Labs et al.; Analysis of Solid Phase Debris from Laser Angioplasty: Potential Risks of Atheroembolism; Feb. 1988, pp. 326–335.

*Interventional Radiology*, Coleman et al: Atheroblation with Kensey Catheter: A Pathologic Study; Feb. 1989, pp. 391–394.

*Cardio*, Barbara J. Dwyer: Atherectomy Devices: A Clinical Comparison; Apr. 1989, pp. 123–129.

*Mayo Clinic Proceedings*, Kaufmann et al.: Coronary Atherectomy: First 50 Patients at the Mayo Clinic; Jul. 1989, pp. 747–752.

*RöFo*, Schild e al.; Klinische Erfahrugen mit dem Kensey–Katheter–System–Kompltationen und Ergbnisse, Feb. 1990, pp. 168–172.

*Catherization and Cardiovascular Diagnosis*, Titus et al.: Distal Embolization during mechanical Thrombolysis: Rotational Thrombectomy Vs. Ballon Angioplasty; 1990, pp. 279–285.

*Mayo Clinic Proceedings*, Holmes, Jr. et al.: Advances in Interventional Cardiology; Apr. 1990, pp. 565–583.

*AJNR*, Robert Ferguson, Getting it Right the First Time, Sep./Oct. 1990, pp. 565–583.

*Cardiovasc Intervent Radiokl*, Matsumoto et al.: Percutaneous Management of Emboli Associated with hot Tip Laser–Assisted Angioplasty, 1990, pp. 13:71–74.

*AJNR*, Theron et al.: New Triple Coaxial Catheter System for Carotid Angioplasty with Cerebral Protection, Sep./Oct. 1990, pp. 11:869–874.

*J Endovasc Surg.* Henry et al., Angioplasty and Stenting of the Extracranial Carotid Arteries; 1998, pp. 5:293–304.

*Texas Heart Institute Journal*, Diethrich, Cartoid Angioplasty and Stenting; 1998, vol. 25, No. 1 , pp. 1–9.

*J Endovasc Surg.*, Henry et al. Cartoid Stenting with Cerebral Protection: First Clinical Experience Using the Percu-Surge GuardWire System, 199, pp 6:321–331.

Various Embolic Protective Devices, Summary on 2 sheets (4 pages).

Simon Nitinol Filter, 2 Sheets (4 pages) of Bard Advertisement handout.

Advanced Talent System, 1 sheet, 1 page handout by World Medical Manufacturing Coroporation.

Proximal Grab Method, Regarding Amplatz "Goose Neck"™ Snares & Microsnares, 2 sheets, 4 pages. Handout of Microvena Corporation.

Rotablator Reference Guide 2, sheets, 1 page on each sheet, Copyright 1998.

*Intervention Cardiology*, Walter Alexander,; Promise Seen in Carotid Treatments, May 2000, p. 21.

*Can Med Assoc J*, D. Lynn Doyle: Update on laser angioplasty, 1990, pl 1391.

\* cited by examiner 36  38

36  38

36  38

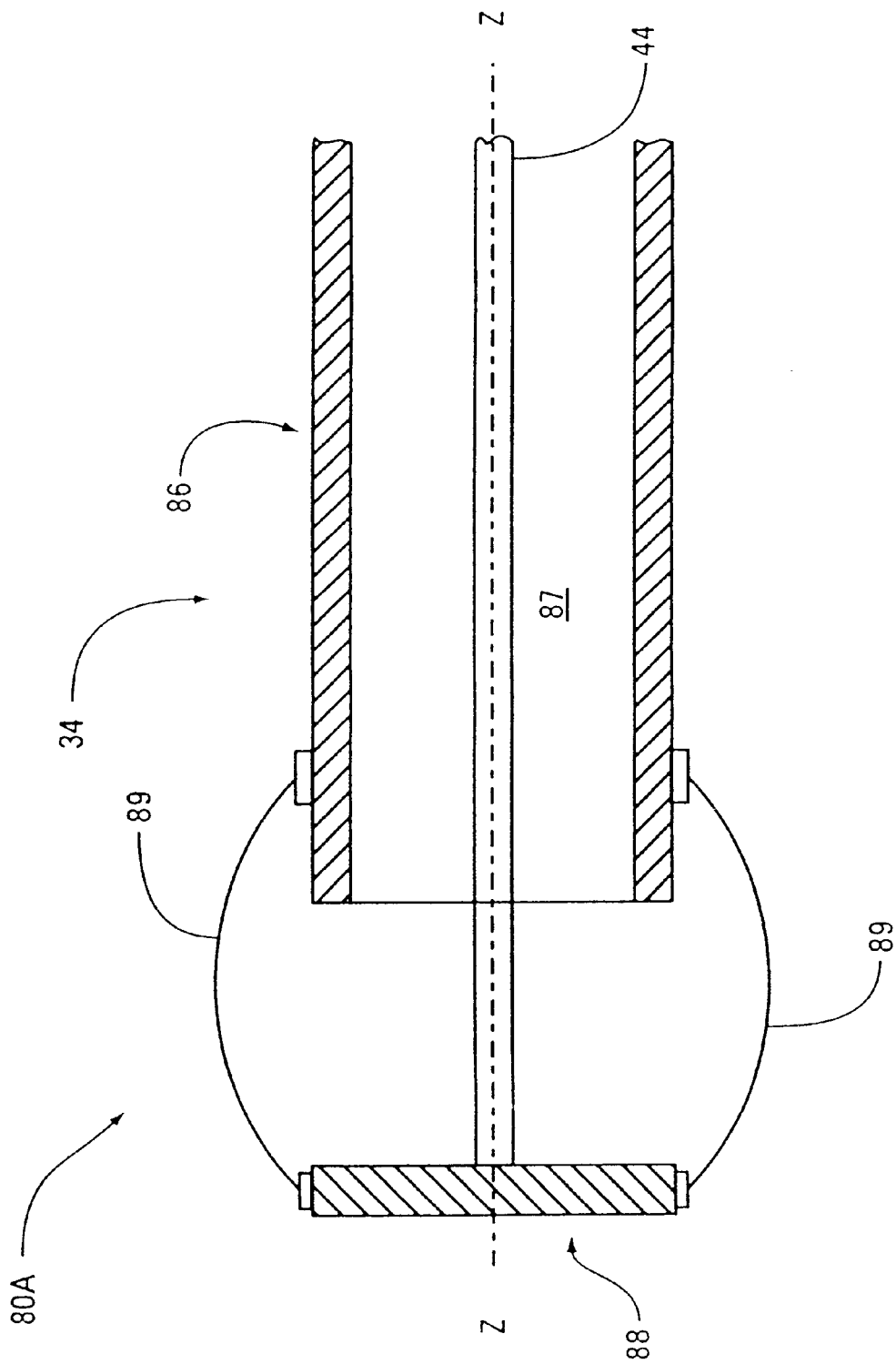

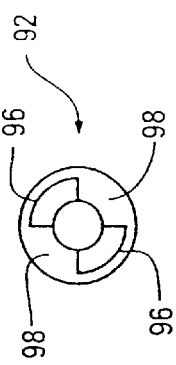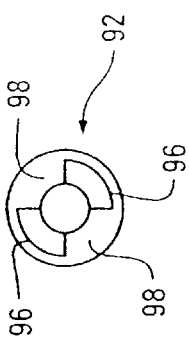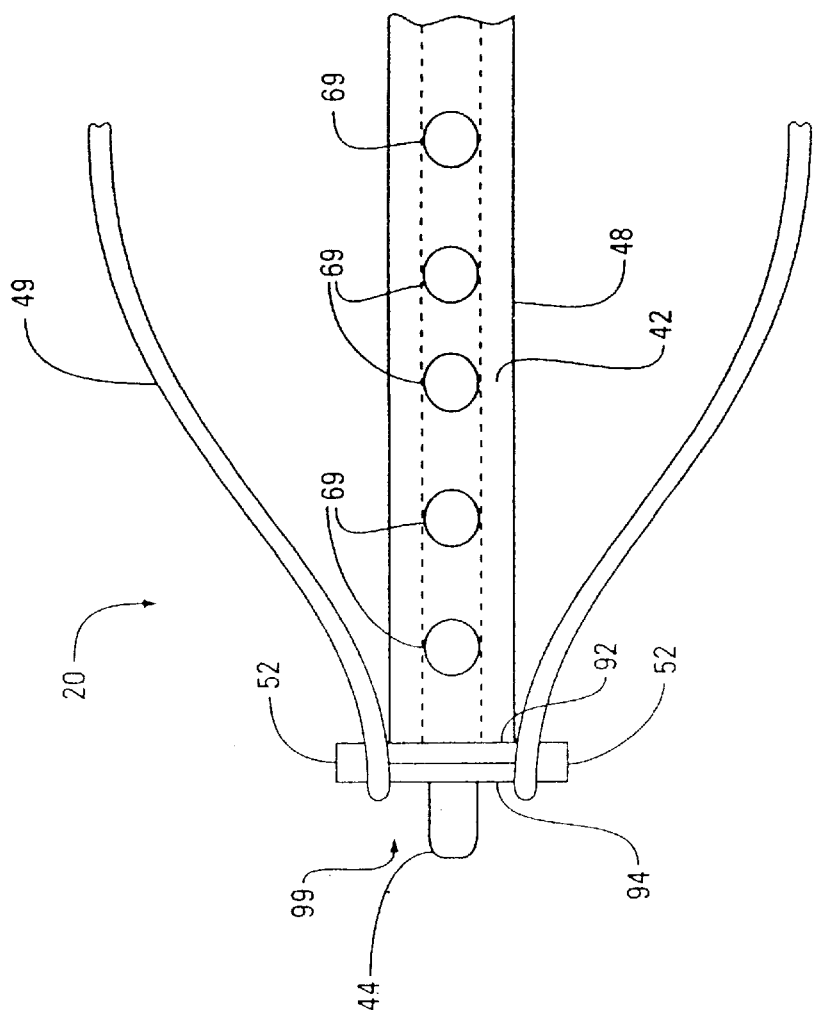

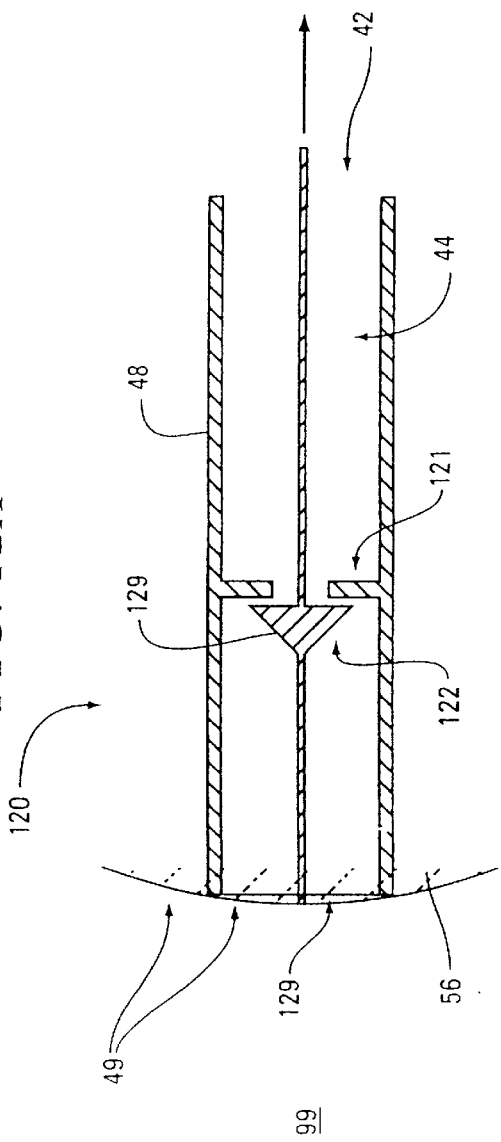
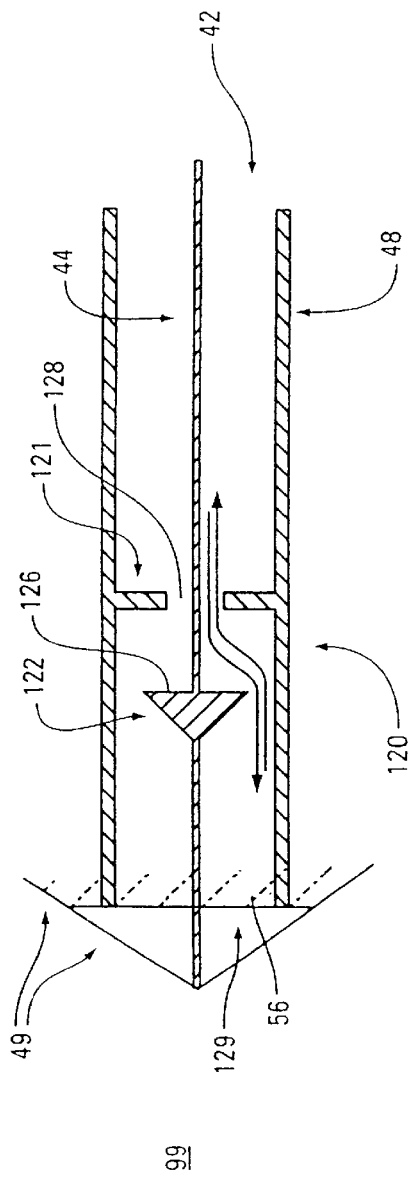
FIG. 12A
FIG. 12B

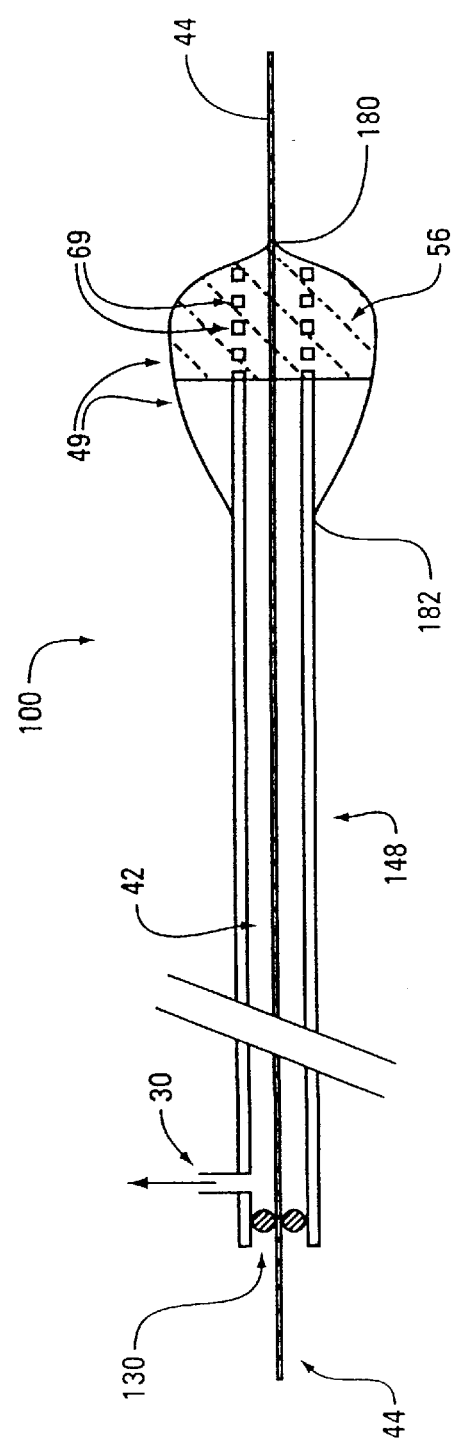
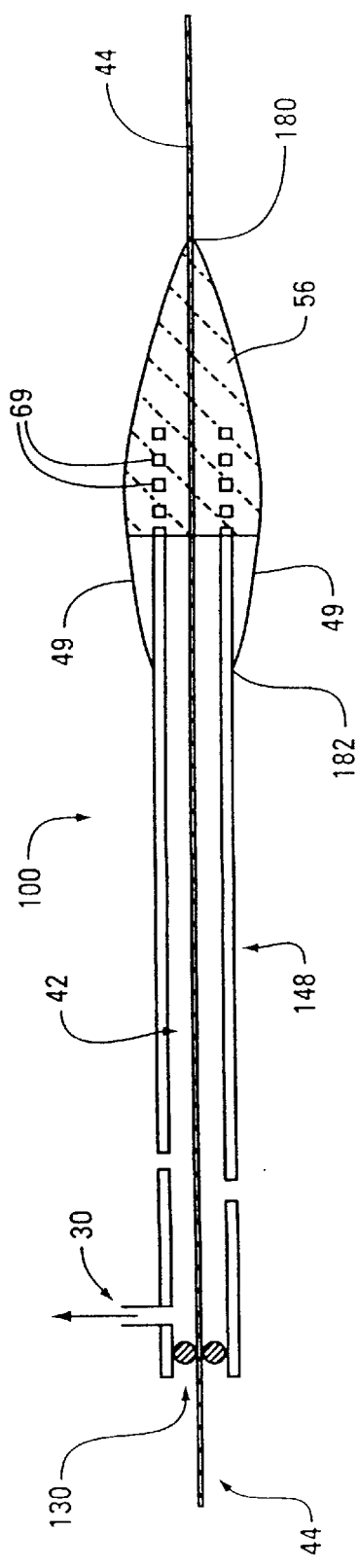

EMBOLIC PROTECTION DEVICE HAVING EXPANDABLE TRAP

CROSS-REFERENCE TO RELATED APPLICATION(S)

This application is a continuation of U.S. patent application Ser. No. 09/495,833, filed Feb. 1, 2000, now issued as U.S. Pat. No. 6,443,926, issued on Sep. 3, 2002, which is hereby incorporated by reference in its entirety.

FIELD OF THE INVENTION

This invention relates to an angioplasty device for compressing and/or removing atherosclerotic plaques, thromboses, stenoses, occlusions, clots, potential embolic material and so forth (hereinafter "obstructions") from veins, arteries, vessels, ducts and the like (hereinafter "vessels"). More particularly, the invention relates to a total capture angioplasty device and trap capable of use in small and large diameter vessels and vessel-like structures.

BACKGROUND OF THE INVENTION

Angioplasty devices are used to treat a wide variety of conditions and to perform a wide variety of procedures, including without limitation: congenital or acquired stenoses or obstructions; percutaneous aspiration thromboembolectomy; cerebral embolization; congenital or acquired obstruction or stenosis of the aorta, renal, coronary, pulmonary, iliac, femoral, popliteal, peroneal, dorsalis pedis, subclavian, axillary, brachial, radial, ulnar, vertebral, cerebral and/or cerebellar artery or any other accessible artery or their ramifications; congenital or acquired obstruction or stenosis of the superior vena cava, inferior vena cava, common iliac, internal iliac, external iliac, femoral, greater saphenous, lesser saphenous, posterior tibial, peroneal, popliteal, pulmonary, coronary, coronary sinus, innominate, brachial, cephalic, basilic, internal jugular, external jugular, cerebral, cerebellar, sinuses of the dura mater and/or vertebral vein or any other accessible vein or their ramifications; atheromatous lesions of any graft or its ramifications; obstructions or stenoses of connections between and among grafts, veins, arteries, organs and ducts; vena caval bleeding; congenital or acquired intracardiac obstructions, stenoses, shunts and/or aberrant communications; congenital or acquired cardiovascular obstructions, stenoses and/or diseases; infusion of thrombolytic agents; thromboembolic phenomena; diagnostic catheterization; removal of clots; intrahepatic and/or extrahepatic biliary ductal obstructions (e.g., stones, sediment or strictures); intravascular, intracardiac and/or intraductal foreign bodies; renal dialysis; congenital and acquired esophageal and/or gastrointestinal obstructions and/or stenoses; non□organized atheromata; dialysis fistula stenosis; ruptured cerebral aneurysm; arterio□arterial, arterio-venous and/or veno-venous fistulae; ureteral obstructions (e.g., stones, sediment or strictures); fibromuscular dysplasia of the renal artery, carotid artery and/or other blood vessels; and/or atherosclerosis of any accessible artery, vein or their ramifications. Such procedures may be performed in both humans and in other applications.

Conventional angioplasty devices generally consist of a catheter containing a balloon-like member that is inserted into an occluded vessel. Expansion of the balloon at the obstruction site crushes the obstruction against the interior lining of the vessel. When the balloon is retracted, the obstruction remains pressed against the vessel wall and the effective diameter of the vessel through which fluid may flow is increased at the site of the obstruction. Examples of angioplasty devices incorporating a balloon are shown in U.S. Pat. Nos. 4,646,742; 4,636,195; 4,587,975; and 4,273,128.

Other conventional angioplasty devices have been developed that incorporate expandable meshes or braids, drilling or cutting members, or lasers as a means for removing an obstruction. Examples of these angioplasty devices are illustrated by U.S. Pat. Nos. 4,445,509; 4,572,186; 4,576,177; 4,589,412; 4,631,052; 4,641,912; and 4,650,466.

Many problems have been associated with these angioplasty devices. Perhaps the most significant problem is the creation of particulate matter during the obstruction removal procedure. Recent ex vivo studies have demonstrated that huge numbers of emboli are produced on inflation and on deflation of the angioplasty balloon during dilation of a stenotic lesion. See Ohki T. Ex vivo carotid stenting, (Presentation) ISES International Congress XI, Feb. 11, 1998. These particles are released into the fluid flowing through the vessel and can lead to emboli, clots, stroke, heart failure, hypertension and decreased renal function, acute renal failure, livedo reticularis and gangrene of the lower extremities, abdominal pain and pancreatitis, cerebral infarction and retinal emboli, tissue injury, tissue death, emergency bypass surgery, death and other undesirable side effects and complications. Regardless of the type of angioplasty device used, a substantial number of particles will be generated.

Even very small particles can cause significant harm. The cross-sectional diameter of normal capillaries varies for different parts of the body and may be comprised of vessels as small as $2.0-3.5\mu$ for very thin capillaries or $3.5-5.0\mu$ for moderately thin capillaries. Accordingly, any particles that exceed these sizes can lodge inside the vessel. Furthermore, in the case of the heart, approximately 45% of the capillaries are closed at any given time, so that any particle, no matter how small, dislodged into this organ is liable to capture. Accordingly, it has become apparent that distal embolization presents a formidable threat.

One partial solution to the above-noted problems is disclosed in U.S. Pat. No. 4,794,928 to Kletschka. This angioplasty device incorporates a trap/barrier for trapping and removing particles that break away from the treatment sight. This device is desirable because it can prevent physiologically significant particles from escaping from the obstruction site, thus preventing the occurrence of unfavorable side effects from angioplasty treatment and procedures. One problem with this design, however, is that it is difficult to simultaneously provide an angioplasty device that is small enough to be used in very small and medium sized arteries, and/or in severely occluded vessels (i.e., vessels having a 90% or greater stenosis), and that has sufficient suction to remove the particulate matter.

Another partial solution to the above noted problems uses multiple catheters. These devices require that the doctor first deliver a "blocking" catheter to the target region such that its occlusion balloon is distal to the treatment site. The doctor then loads a second "balloon" catheter over the blocking catheter and performs the angioplasty procedure. The second catheter is then removed and a third catheter is loaded in its place over the blocking catheter. The third catheter can be used to aspirate blood from the treatment site. One problem with this design, however, is that it does not provide a means for capturing particles that are too large to fit within the suction lumen. Another problem is that this design requires a complex and relatively lengthy operational procedure, which can lead to neurological complications. In addition, particulate matter may also escape or be pulled from the treatment site when the catheters are switched and when the blocking balloon is deflated. Even when combined with suction, the risk exists that particles too large to be removed through the suction conduit will be delivered distally from the forward thrust of the blood flow as the blocking balloon is deflated.

Still another partial solution uses a porous hood that allows blood to pass. The hood, attached to the guidewire with struts, is held in a collapsed state within the angioplasty catheter. The hood deploys when pushed beyond the tip of the restraining catheter. Withdrawing the hood within the catheter closes the trap. These devices, however, do not provide suction and require multiple catheters. In addition, small particles may pass through the porous hood.

FIG. 1 illustrates the problems associated with obtaining the size of conduits necessary to do just the desired insertion, inflation, and suction tasks.

FIG. 1 is a cross section of a five French catheter 10. A standard, 150 centimeter long, catheter may need a suction lumen 12 with a diameter of about 0.025 inches in order provide sufficient suction at its operational end to cope with debris released from a large atheromatous plaque. The catheter may also require an inflation/deflation lumen 14 with a diameter of about 0.015 inches, to inflate an angioplasty balloon and a centered guidewire lumen 16 having a diameter of about 0.035 inches to position the device. As can be seen, these lumens significantly interfere with each other. An additional mechanism to open and close a blocking/capturing device will further encroach on allocatable space.

Clearly, there is a need for an improved angioplasty device for use in small diameter and/or severely occluded vessels that can prevent substantially all physiologically significant particles from escaping from the obstruction site, thus preventing the occurrence of unfavorable side effects from the angioplasty treatment and procedures. There is also a need for a small diameter angioplasty device that can provide aspiration, blocking, and capturing capabilities. In addition, there is a need for an improved particle trap that can prevent substantially all physiologically significant particles from escaping from the obstruction site and that can fit within, and be actuated by, a small diameter catheter bundle.

BRIEF SUMMARY OF THE INVENTION

The present invention provides an apparatus for use in angioplasty procedures or other medical, veterinary, non-medical or industrial applications where removal of an obstruction from a vessel or vessel-like structure could produce particles, which, if allowed to remain in the vessel, could cause undesirable complications and results. The present invention is particularly suited for use in small diameter vessels and/or in severely occluded vessels, and can prevent substantially all physiologically significant particles from escaping from the obstruction site. Particles smaller than the width of the suction lumen are removed by aspiration in some embodiments, while the larger particles are captured beneath a contractible hood and removed when the catheter is withdrawn. Some embodiments also have a provision for aspirating debris generated as the angioplasty device is insinuated through a stenosis.

One aspect of the present invention is an angioplasty device for removing an obstruction from a vessel or vessel-like structure. One embodiment of this angioplasty device comprises a catheter for insertion into a vessel-like structure and a trap operably connected to the catheter and to a rotatable member, such as a fixed guidewire or a catheter, wherein a rotation of the rotatable member relative to the catheter actuates the trap. Some embodiments of this angioplasty device may also comprise a flexible strut fixedly connected to the catheter and to the trap. This flexible strut may expand and contract the trap by moving between a helically twisted position and an arcuately expanded position.

Another aspect of this invention is a trap for selectively blocking a vessel or vessel-like structure. One embodiment comprises a rotatable member, such as a fixed guidewire or a catheter, that actuates a flexible strut between an arcuately expanded position and a helically twisted position, and a membrane operably connected to the flexible strut. These embodiments may further comprise a first ring that fixedly connects the rotational member to the flexible strut and a second ring that fixedly connects the flexible strut to a catheter. In addition, the proximal portion of the flexible struts can be inserted into the wall of the catheter in place of or in addition to the second ring.

Another aspect of the present invention is a method of making a particle trap adapted for removing an obstruction from a vessel-like structure. One embodiment comprises the acts of operably connecting a plurality of flexible struts to an outer surface of a catheter, the catheter containing a rotatable member; operably connecting the plurality of flexible struts to the rotatable member; and operably connecting a membrane to the plurality of flexible struts.

Another aspect of the present invention is a device for removing an obstruction from a vessel-like structure. One embodiment comprises a catheter for insertion into a vessel-like structure, the catheter having a catheter wall and a moveable member, and a trap operably connected to the catheter wall and to the moveable member. Relative motion between the catheter wall and the moveable member actuates the trap. This relative motion may be a relative rotation or a relative translation.

Another aspect is a catheter bundle for insertion into a vessel-like structure. The catheter bundle in this embodiment defines a balloon adapted to compress an obstruction against the vessel-like structure; a trap adapted to selectively block the vessel-like structure; an inflation lumen in operable communication with the balloon; and a suction lumen in operable communication with the trap. This catheter bundle has a diameter of less than about twenty French, with some embodiments having a diameter of less than about; five French.

Another aspect of the present invention is a type of angioplasty procedure. One embodiment of this procedure comprises the acts of inserting a catheter into the vessel-like structure, the catheter including a trap and an actuator; positioning the trap in a downstream direction from an obstruction; moving the actuator in a first direction, thereby opening the trap; and moving the actuator in a second direction, thereby closing the trap. This procedure may further comprise the act of removing the obstruction from the vessel-like structure, thereby producing at least one particle. The at least one particle may be removed from the vessel-like structure using a suction lumen, the trap, or a combination thereof.

Three additional aspects of the present invention are a modular trap for an angioplasty device, a guidewire for use in a medical device, and an angioplasty device having a valve. One modular trap embodiment comprises a trap adapted to selectively block a vessel-like structure; and a coupling device that couples the trap to the angioplasty device. One guidewire embodiment comprises a guidewire wall defining a proximal opening, a distal opening, and an annular passageway, wherein the annular passageway fluidly connects the proximal opening to the distal opening. One angioplasty device embodiment; with a valve comprises a first lumen, and a valve adapted to selectively block the first lumen.

One feature and advantage of the present invention is that it can provide a small diameter angioplasty device that can trap and remove substantially all physiologically significant particles. Another feature and advantage of the present invention is that it can provide aspiration, blocking, and capturing capabilities in a single catheter. Yet another feature and advantage is that the present invention maximizes the amount of suction per unit size, thus providing the doctor with more suction in larger vessels than presently available. These and other features, aspects, and advantages of the present invention will become better understood with reference to the following description, appended claims, and accompanying drawings.

BRIEF DESCRIPTION OF THE DRAWINGS

FIG. 10 is a detailed side plan view of an embodiment having a flexible membrane extension system.

FIG. 11A is a side plan view of an embodiment capable of providing suction during insertion.

FIGS. 11B and 11C are side plan views of two disks for use with the embodiment in FIG. 11A.

FIGS. 12A and 12B are sectional views of an alternate valve embodiment.

FIG. 21 is a sectional view of a trap actuated by a relative translation, showing the trap in an arcuately expanded position.

FIG. 22 is a sectional view of the trap in FIG. 21, showing the trap in a contracted position.

DETAILED DESCRIPTION

Figure 2:
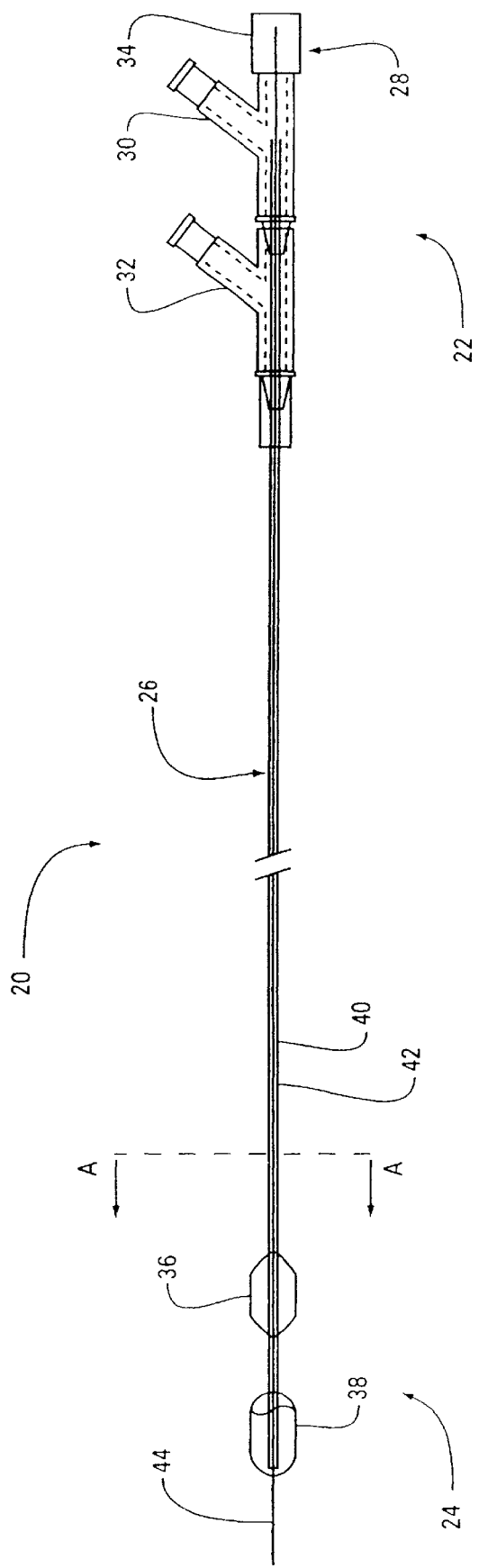
FIG. 2 is a side view of one embodiment of the angioplasty device of the present invention.

FIG. 2 is a side plan view of one embodiment of the angioplasty device 20 of the present invention. This angioplasty device 20 comprises a flexible catheter 26 having a proximal end 22, a distal end 24, and a generally circular cross section. The proximal end 22 of the catheter 26 is connected to a branched housing 28 that contains a suction port 30, an inflation port 32, and a guidewire port 34. The distal end 24 of the catheter 26 is connected to an angioplasty balloon 36, and a trap/barrier 38. As will be described in more detail with reference to FIG. 4, the flexible catheter 26 contains an inflation/deflation lumen 40, a suction/vacuum lumen 42, and a flexible guidewire 44.

In operation, distal end 24 of the angioplasty device 20 may be inserted into a vessel at any point in relation to the treatment site that is consistent with the desired treatment protocol. The balloon 36 is then aligned with the obstruction using methods known in the art, such as a radiopaque contrast solution, so that the trap 38 is situated in a position downstream from the obstruction site with the opening of the trap 38 positioned so that the fluid will flow into it and beneath the hood/membrane.

After positioning, the trap 38 may be expanded so that it forms a seal against the inner lining of the vessel. This seal will prevent physiologically significant particles from leaving the treatment site. A fluid, air, or other expansion medium may be then injected into the device 20 through the inflation port 32 and may be delivered through the lumen 40 to the balloon 36. The balloon 36 may then be expanded to perform its function. Alternatively, the balloon 36 and the trap 38 may be expanded simultaneously or the balloon could be expanded before the trap 38. As the balloon 36 is expanded, the obstruction is crushed against the inner diameter of the vessel, which increases the area through which fluid can flow. Crushing of the obstruction, however, creates particles that may break free on either side of the balloon 36.

When the vessel is living tissue (e.g., a human or animal vein, artery or duct) the balloon 36 may be inflated to a pressure ranging from approximately three to fifteen atmospheres, or more, depending on the application. The proper pressure will be dependant on the treatment protocol, the type of organism being treated, the type of vessel being treated and the material from which the balloon is constructed. Appropriate expansion pressures for a given situation will be known to those skilled in the art.

The balloon 36 may then be partially retracted so that a pressure differential between the vessel and the suction lumen 42 can draw any resulting particles toward the trap 38. Particles are either drawn into and through the catheter 26 or lodged in the trap 38 such that, when the trap 38 is retracted, the particles are trapped inside.

Figure 3A:
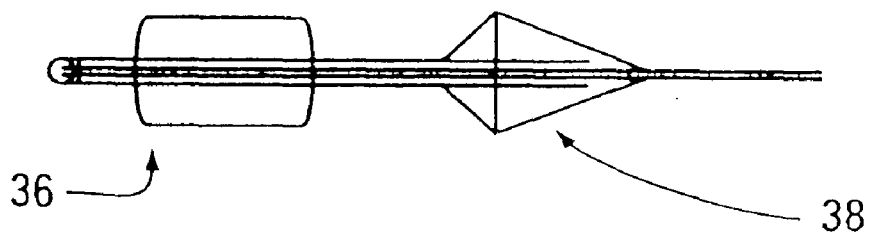
FIGS. 3A–3C are side plan views of different trap embodiments.
Figure 3B:
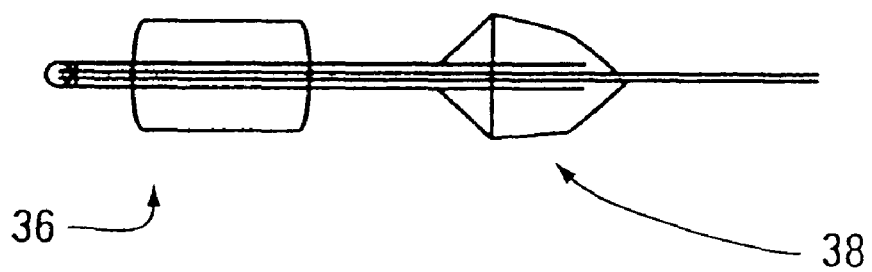
Figure 3C:
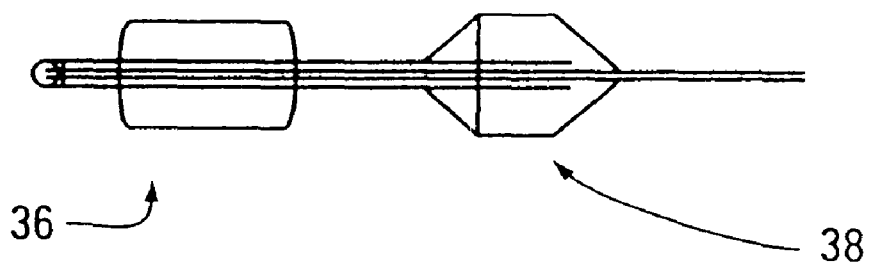

The trap 38 in this embodiment may assume any final shape as long as a substantial seal is achieved with the inner lining of the vessel to be treated and so long as the shape facilitates entrapment of the particles. FIGS. 3A–3C show three possible trap 38 embodiments. In particular, FIG. 3A shows a generally conically shaped trap 38, FIG. 3B shows a more or less "egg" shaped trap 38, and FIG. 3C shows a more or less oval shaped trap 38. Other trap 38 shapes and configurations are also within the scope of the present invention. In addition, the trap 38 and the balloon 36 may be situated with respect to each other in any configuration that allows the trap 38 to achieve a seal with the inner vessel lining and to trap particles when expanded. This includes, without being limited to, configurations in which the relative locations of the balloon 36 and the trap 38 are reversed. In contrast with the "antegrade" embodiments depicted in FIGS. 2 and 3A–3C, these "retrograde" embodiments would allow insertion of the angioplasty device from a point "downstream" from the treatment site.

Those skilled in the art will recognize that the balloon 36 in this embodiment serves as an operative member and may be replaced by any means known in the art, or later developed in the art, for removing or compressing an obstruction. Thus, as used throughout this specification and the claims, the terms "balloon" and "operative member" encompass any means for removing or compressing an obstruction, including but not limited to the means represented by U.S. Pat. Nos. 4,646,742, 4,636,195, 4,587,975, 4,273,128, 4,650,466, 4,572,186, 4,631,052, 4,589,412, 4,445,509, 4,641,912 and 4,576,177, the disclosures of which are incorporated herein by reference, and which include meshes, cutting rotors, lasers, and treatment agents. Each type of operative member will have its unique control mechanism that, in the case of a balloon, fills it or, in the case of a laser or cutting rotor, turns it on. Although the balloon and its associated filling or expansion system will be used throughout the specification as an example of an operative member and its associated control means, it is to be understood that any available operative member and its control means could be substituted in many of the embodiments discussed herein. Thus, references to "expansion" and "retraction" of the balloon should be understood, by inference, to refer to activating and deactivating whatever operative member is incorporated into a given device 20.

Figure 4:
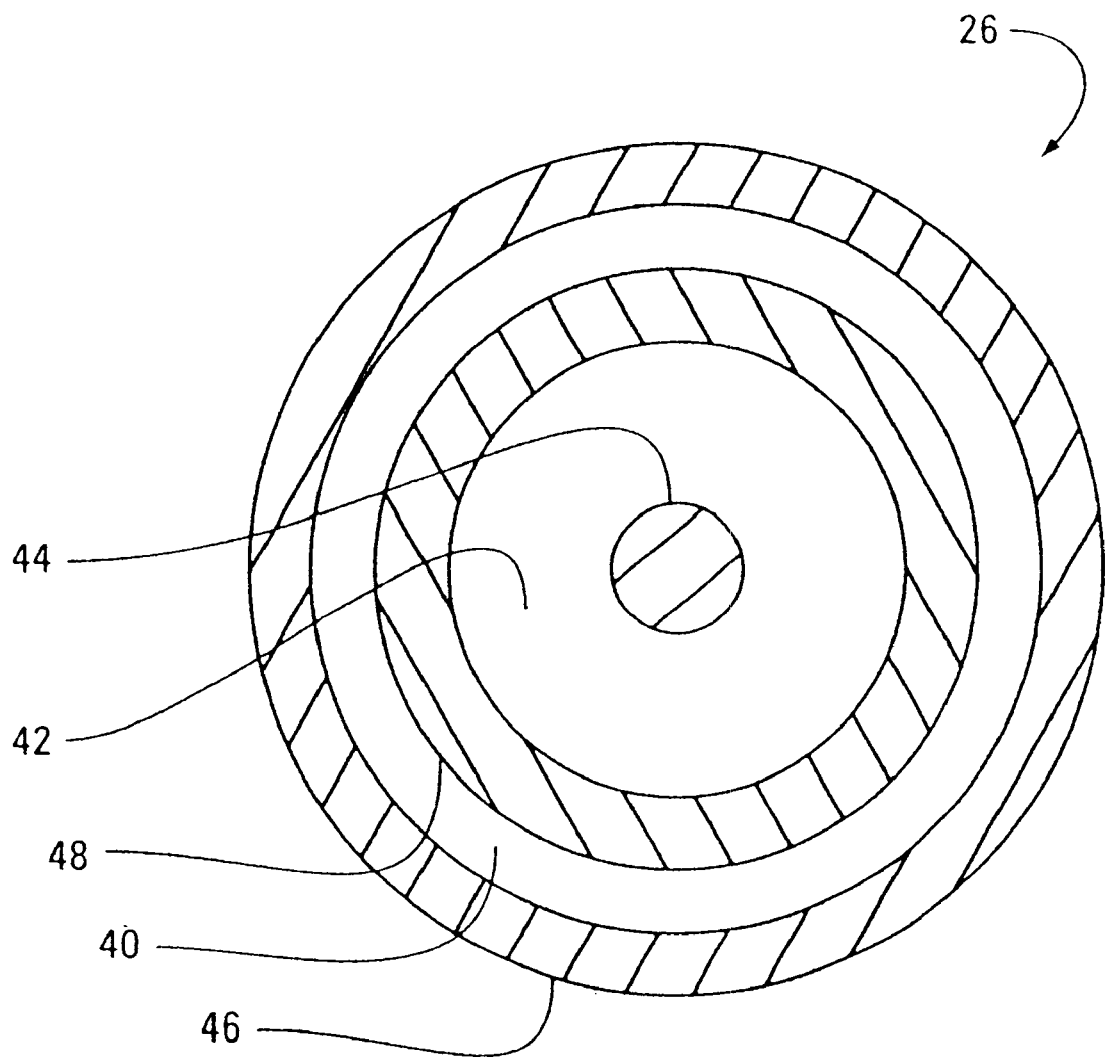
FIG. 4 is a sectional view of the embodiment depicted in FIG. 2 taken along the line AA.

FIG. 4 is a sectional view of the catheter 26 in FIG. 2 taken along line AA. The catheter 26 includes an outer wall 46, the inflation/deflation lumen 40, an inner wall 48, the suction lumen 42, and the guidewire 44.

The inner wall 48 and the outer wall 46 may be made from any relatively flexible material. When used in medical applications it is desirable, however, that the chosen material be approved for use in medical devices, be compatible with standard sterilization procedures, and be able to withstand the balloon's 36 inflation pressure without undue expansion in the radial direction. One suitable material is nylon. However, other wall materials are within the scope of this invention. In some embodiments, the inner wall 48 and the outer wall 46 comprise the same material. These embodiments may be desirable because they are generally easier to manufacture. However, embodiments where the inner wall 48 is made from a different material than the outer wall 46 are within the scope of this invention. In addition, the inner wall 48 may be reinforced in some embodiments with a metallic or plastic stent, strut, coil, or similar member, either in sections or for the full extent. These reinforcement members may also be embedded into the catheter wall.

The relative sizes and positions of the outer wall 46, the inflation/deflation lumen 40, the inner wall 48, the suction lumen 42, and the guidewire 44 are arbitrary. However, it is desirable to make the inflation/deflation lumen 40 and the suction lumen 42 as large as possible so that they can provide greater suction to the distal end 24, and ease of inflation and deflation of the angioplasty balloon (when that is the operative member). That is, the maximum vacuum that may be applied through the suction port 30 is limited by the wall materials. This maximum available vacuum is reduced by frictional losses between the proximal end 22 and the distal end 24. Because frictional losses in a closed channel are inversely proportional to the channel's cross sectional area, increasing the cross sectional area will increase the vacuum available at the distal end 24.

One method of increasing the cross sectional areas of the inflation/deflation lumen 40 and the suction lumen 42 is to make the outer wall 46, the inflation/deflation lumen 40, the inner wall 48, the suction lumen 42, and the guidewire 44 substantially coaxial. Coaxial arrangements can increase the available cross sectional area because, for a circle:

$$dA/dr = 2\pi r.$$

Thus, a lumen located near the outside of the catheter 26 will have a larger flow area than will a lumen that is located near the interior of the catheter 26, even if both lumens consume the same amount of distance between the walls. It was discovered that the increased flow area resulting from the coaxial arrangement can overcome its increased surface area.

Embodiments with coaxial lumens may be particularly desirable if the inner wall 48 helps to form both the inflation/deflation lumen 40 and the suction lumen 42. These embodiments are desirable because the catheter 26 only needs one internal structure to define two lumens. Despite these advantages, however, catheters having two or more inner walls are also within the scope of the present invention. These embodiments may be desirable because they can define additional lumens and can allow one suction lumen 42 to physically move relative to the other inflation/deflation lumen 40.

Accordingly, in one five French catheter 26 embodiment having the coaxial configuration shown in FIG. 4, the outer wall 46 has an outer diameter of 0.066 inches and an inner diameter of 0.056 inches; the inner wall 48 has an outer diameter of 0.0455 inches and an inner diameter of 0.0355 inches; and the guidewire 44 has an outer diameter of 0.012 inches. This provides a suction lumen 42 with a cross sectional area of about 0.0008 square inches. This embodiment is particularly desirable for use in carotid arteries procedures because it provides sufficient suction to remove the obstruction before complications occur and because it is small enough to fit within the artery. Smaller diameter catheters 26 (for example, between two and five French) having smaller suction lumens 42 may be suitable for use in less vital organs, where occlusion time limits are less critical, and in shorter catheters, where frictional losses are less significant. Larger diameter catheters 26 (for example, between five and forty French) having larger suction lumens 42 may be desirable for use in larger arteries, such as the aorta or iliacs, to accommodate the larger blood flow rate, and in longer catheters.

Figure 5:
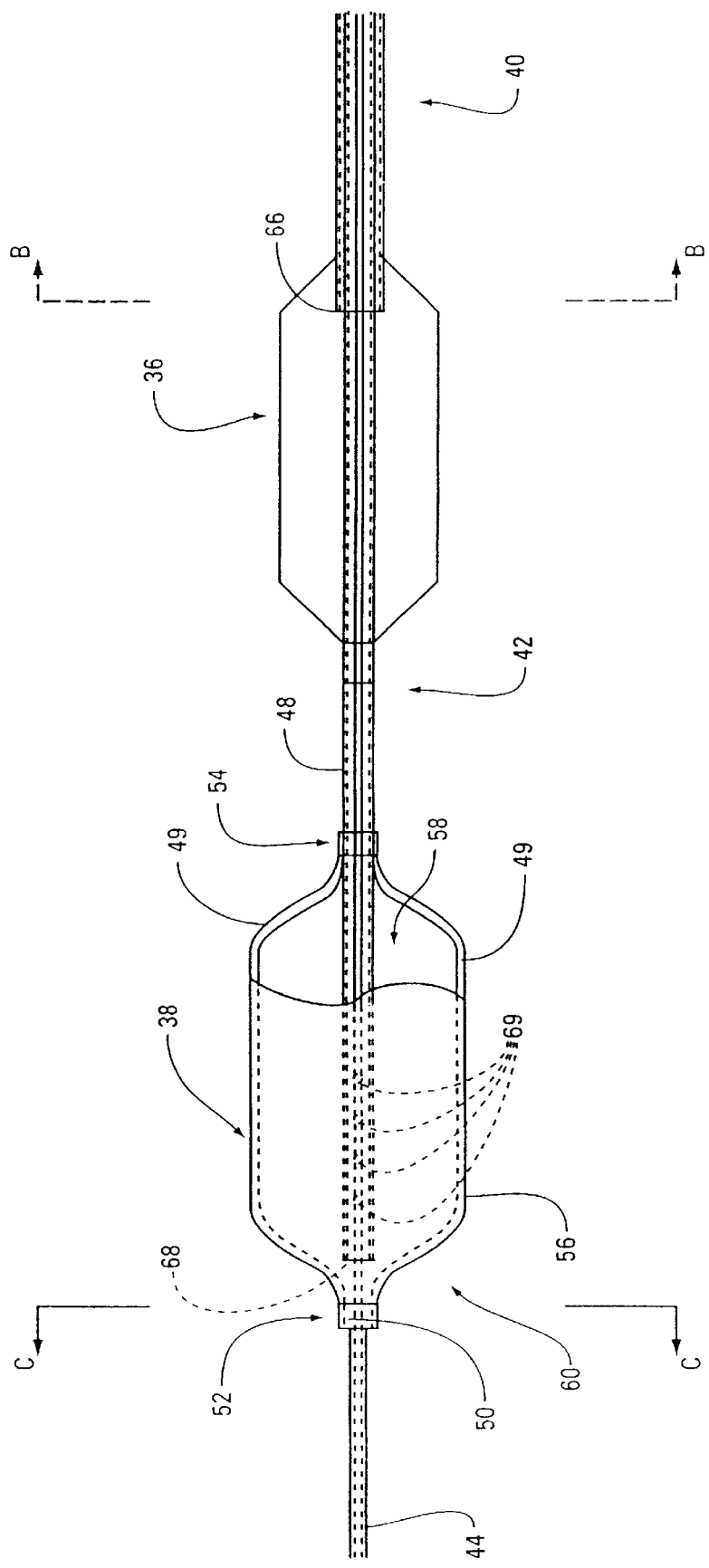
FIG. 5 is a side view of the distal end of the embodiment depicted in FIG. 2.
Figure 28:
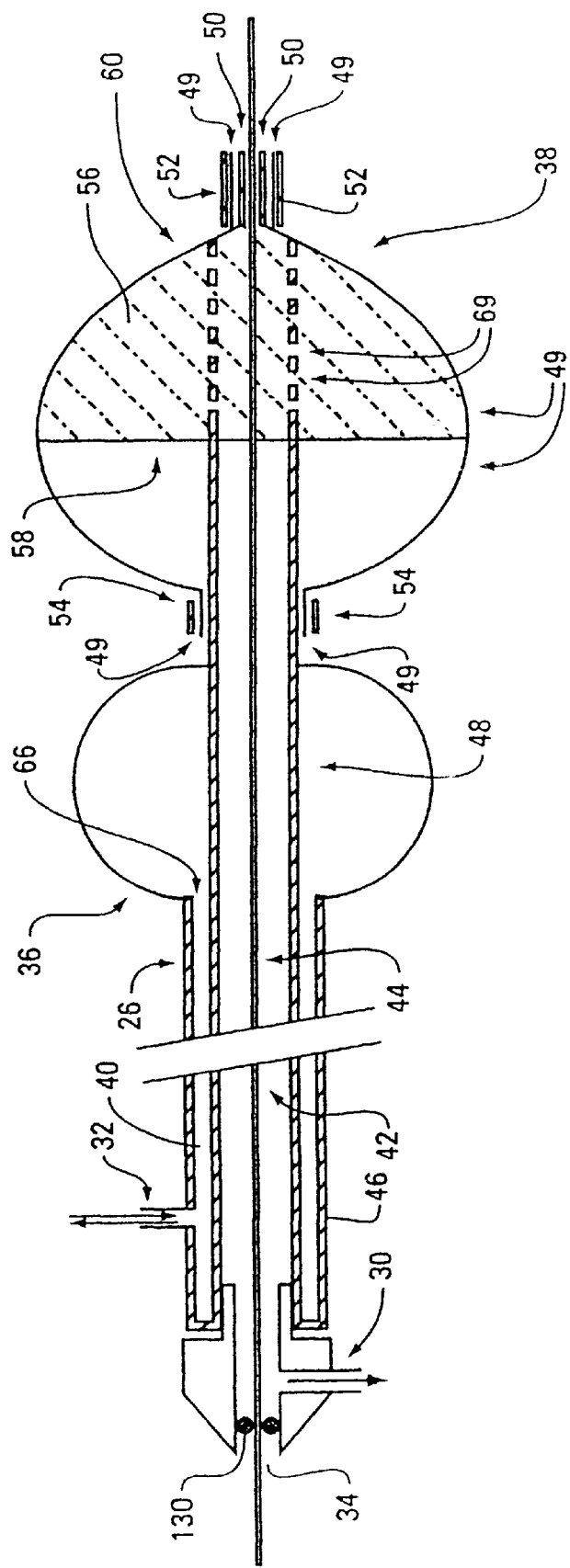
FIG. 28 is a sectional view of the angioplasty device in FIG. 5.

FIGS. 5 and 28 are more detailed views of the distal end 24 of the embodiment in FIG. 2. FIGS. 5 and 28.show that the inflation/deflation lumen 40 (see also FIG. 4) terminates in an opening 66 located inside the balloon 36. This opening 66 allows air, saline solution, or some other inflation medium, to fill the balloon 36 and to bias it radially outward against the obstruction. Similarly, the suction lumen 42 (see also FIG. 4) terminates at a single opening 68 and/or a plurality of pores 69 that are spaced along its length and around its perimeter. These openings 68 and/or pores 69 are used to remove smaller particles from the treatment site and to suck larger particles into the trap 38. Embodiments in which the inflation/deflation lumen 40 terminates immediately at the proximal end of the balloon 36 may be particularly desirable because this minimizes the profile of the balloon 36 in its contracted configuration.

Figure 29:
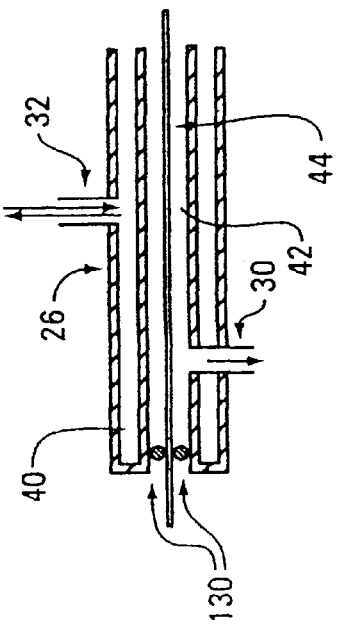
FIG. 29 is a detailed sectional view of an alternate proximal end embodiment.

FIGS. 5 and 28 also show that the trap 38 in this embodiment comprises a plurality of flexible struts 49 in an arcuately expanded position. In one embodiment, these struts 49 are fixedly attached to the guidewire 44 by an inner stainless steel ring 50 and outer stainless steel ring 52, and to the exterior surface of the interior wall 48 by a stainless steel ring 54. A flexible membrane 56 having an open end 58 and a closed end 60 is attached a distal portion of the struts 49. FIG. 29 shows an alternate embodiment in which the branched housing 28 in FIGS. 5 and 28 has been eliminated, with the guidewire going through an O-ring seal 130 in the catheter's proximal end and an integral suction port in direct fluid communication with the suction lumen.

The plurality of flexible struts 49 and the flexible membrane 56 combine to form the trap 38. In some embodiments, flexible struts 49 are longer than the distance between the rings 50, 52 and the ring 54. This causes the flexible struts 49 to function like a single-leaf semi-elliptic beam spring when in their arcuately expanded position. The open end 58 of the flexible membrane 56 in this embodiment is attached to the flexible struts 49 near their area of maximum axial extension. However, the membrane 56 could also be attached proximally or distally to the maximum extension point. The closed end 60 of the flexible membrane 56 is attached to one of the rings 50 and 52. The flexible struts 49 are preferably radially spaced around the catheter 26 so that they can evenly bias the membrane 56 radially outward into contact with an interior wall of a vessel or vessel-like structure.

Rings 50 and 52 fixedly attach the distal end of the flexible struts 49 to the guidewire 44. Similarly, ring 54 fixedly attaches the proximal end of the flexible struts 49 to the exterior surface of the catheter's inner wall 48. Rotating the guidewire 44 relative to the catheter 48 will cause the struts 49 to move between the helically twisted (or "braided") position shown in FIG. 7A and the arcuately expanded position shown in FIG. 7B. That is, rotating the guidewire 44 will cause the distal end of the struts 49 to rotate relative to the proximal end. Because the shortest distance between two points is a straight line, this rotation increases the distance between the proximal end and the distal end. This, in turn, forces the struts 49 to wrap around the inner wall 48 of the catheter 26. Continued rotation of the guidewire 44 will continue to draw the struts radially inward until they lie adjacent to the inner wall 48 of the catheter 26.

Figure 7A:
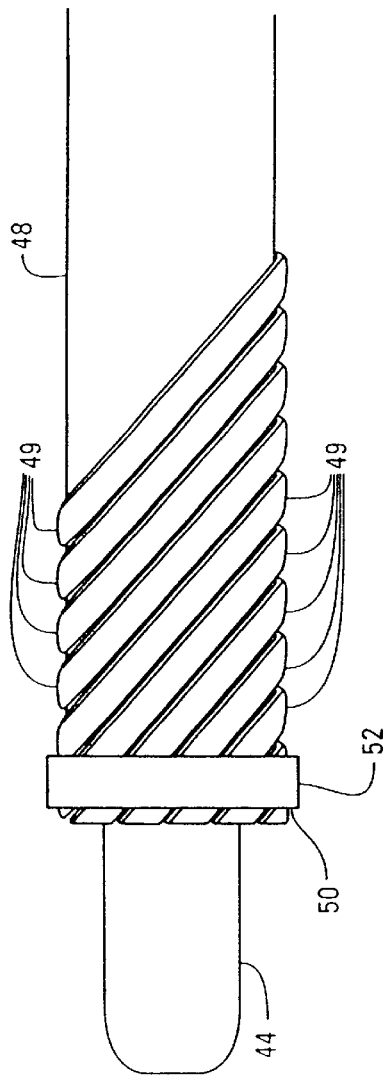
FIG. 7A is a perspective view of an embodiment having a plurality of struts in a helically twisted position, with portions of the struts removed to show the inner catheter wall.
Figure 7B:
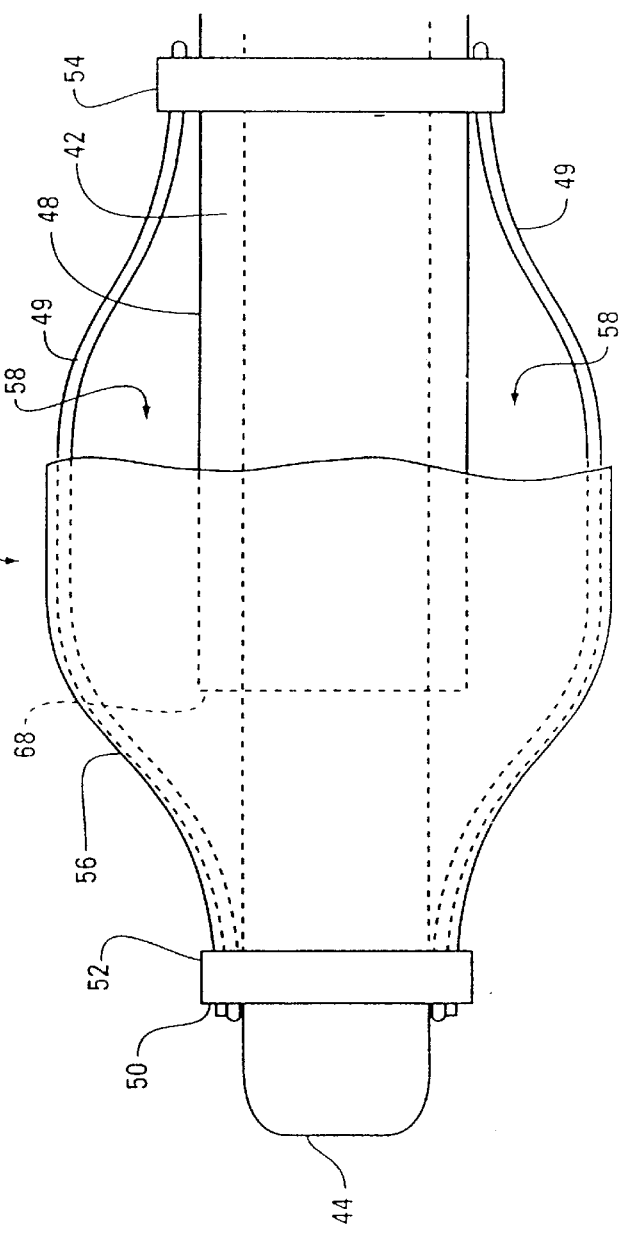
FIG. 7B is a side plan view of an embodiment having a plurality of struts in an arcuately expanded position.

Rotating the guidewire 44 in the opposite direction will cause the struts 49 to untwist, which allows the struts 49 to move back to the arcuately expanded position shown in FIG. 7B. This, in turn, expands the trap 38.

Figure 8:
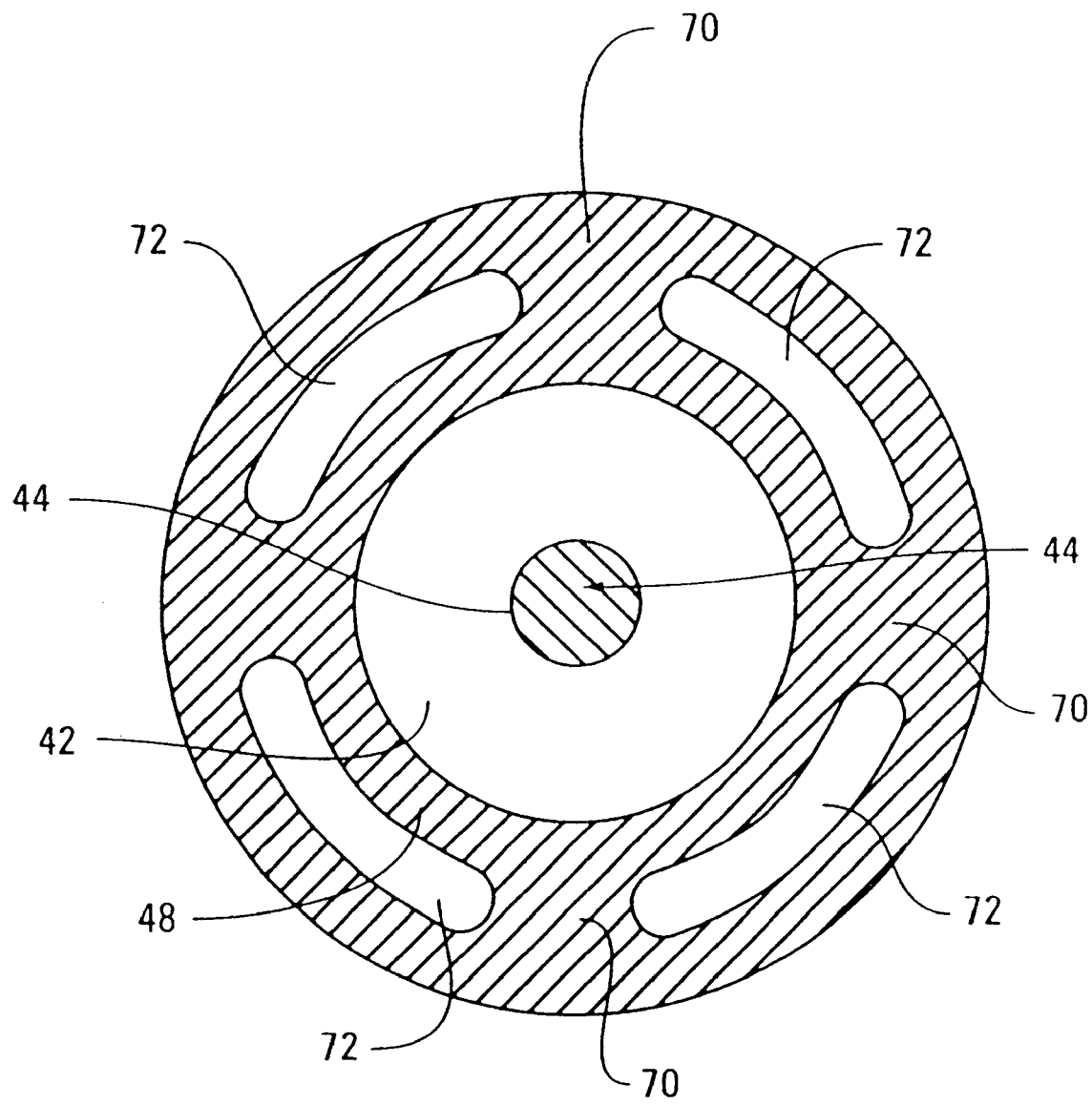
FIG. 8 is a sectional view of a stiffener, taken along the line BB.

FIG. 8 is a sectional view of the angioplasty device 20 in FIG. 5 taken along the line BB. This figure shows four optional stiffening members 70 that connect the inner wall 48 to the outer wall 46. These stiffening members 70 define a plurality of openings 72 that keep the inflation/deflation lumen 40 (see FIG. 4) fluidly connected to the balloon 36 (see FIGS. 5 and 28). These stiffening members 70 are desirable because they give the user something to "push against" when actuating the trap 38. That is, a user expands and contracts the trap 38 (see FIGS. 5 and 28) by rotating the guidewire 44 around its longitudinal axis. The torque used to rotate the guidewire 44 is transferred to the inner wall 48 through the struts 49, which causes the inner wall 48 to twist. The stiffening members 70 couple the inner wall 48 and the outer wall 46. The combined torsional stiffness (or perhaps more accurately, the combined polar moment of inertia) of the inner wall 48 and the outer wall 46 is greater than that of the inner wall 48 alone. In this embodiment, the stiffening members 70 may extend throughout the length of the catheter 26 or may only extend a short distance from the opening 66.

Figure 9B:
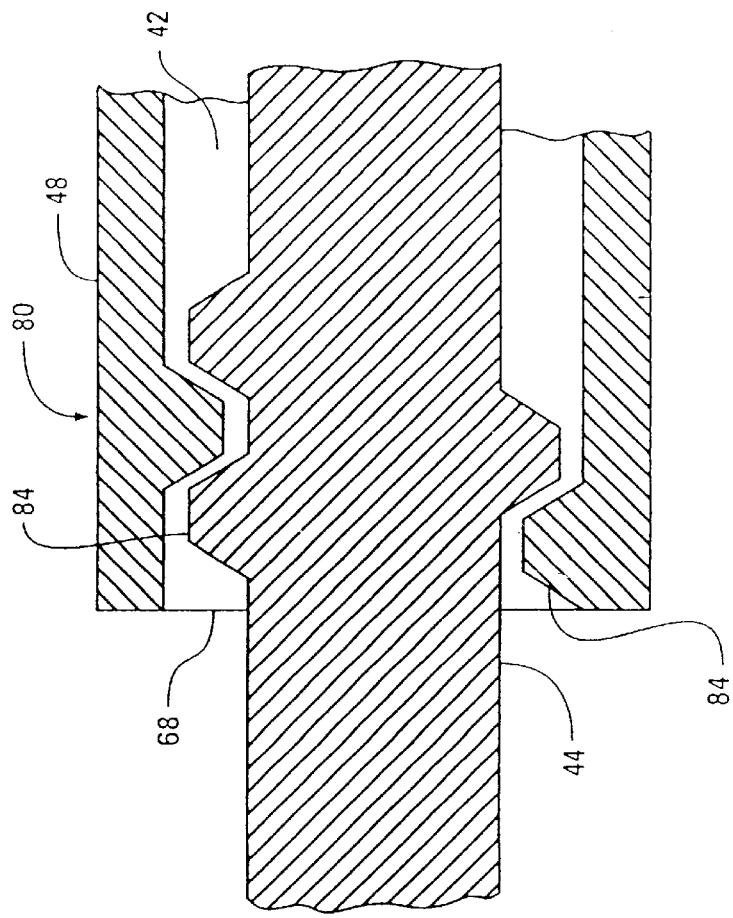
FIGS. 9A and 9B are a sectional view and a side plan view of an embodiment having a screw extension system.
Figure 9A:
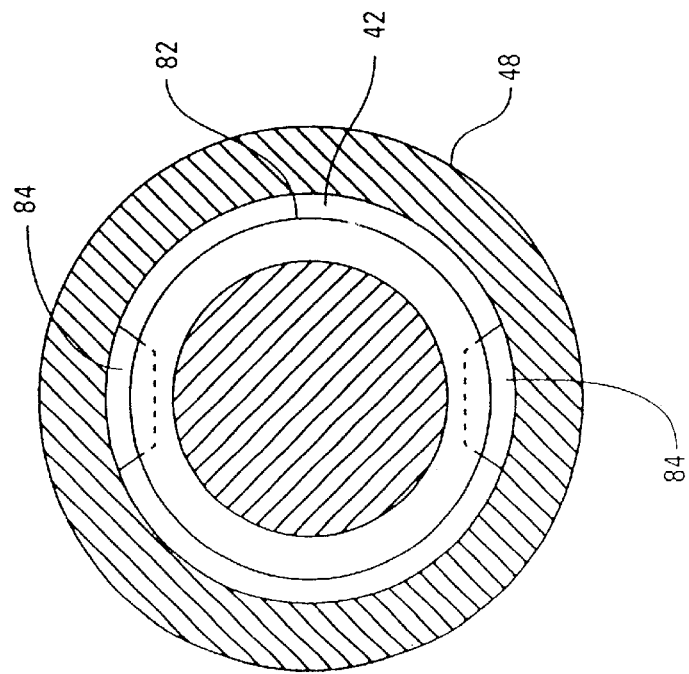

FIGS. 9A and 9B are side plan and sectional views of an angioplasty device 20 having a screw extension system 80 located near the distal end of the suction lumen 42. However, screw extension systems 80 located in other locations, such as within the housing 28, are also within the scope of the present invention. The screw extension system 80 in this embodiment comprises a helical screw thread 82 attached to the guidewire 44 and a pair of offset studs 84 attached to the inner wall 48. The offset studs 84 engage the helical screw thread 82 without blocking the suction lumen 42, which causes the guidewire 44 to move axially inside the suction lumen 42 when rotated. Embodiments having this screw extension system 80 are desirable because it increases the distance between the distal rings 50 and 52 and the proximal ring 54 (see FIGS. 5 and 28), which helps the struts 49 to contract into an orientation that is smooth and tight against the guidewire 44.

FIG. 10 shows a flexible membrane extension system 80*a* that may be used in place of or in conjunction with the screw extension system 80 of FIGS. 9A and 9B. FIG. 10 depicts the proximal end of the guidewire port 34, which comprises a generally cylindrical housing 86 and a generally cylindrical lumen 87 that is fluidly connected to the suction lumen 42 (see FIG. 4). The guidewire 44 runs through the lumen 87 and is connected to a disk shaped handle 88. FIG. 10 also depicts a flexible membrane 89 that is attached to the housing 86 and to the handle 88.

As described with reference to FIGS. 7A and 7B, the user expands and contracts the trap 38 by rotating the guidewire 44 around axis ZZ (see FIG. 10). The guidewire 44, in turn, may be rotated by manually turning the handle 88. Because the membrane 89 is fixed to both the housing 86 and the handle 88, however, this rotation causes the membrane 89 to twist. This twisting motion causes the membrane 89 to bunch together, which pulls the handle 88 in a distal direction towards the housing 86. The handle 88, in turn, pushes the guidewire 44 through the catheter 26.

Embodiments using the flexible membrane extension system 80a in FIG. 10 are desirable because the membrane 89 longitudinally biases the proximal ring 54 relative to the distal rings 50 and 52, thereby helping to actuate the trap 38, and because the membrane 89 helps to seal the suction lumen 42. Preferably, the membrane 89 will comprise materials and dimensions such that the amount of rotation necessary to actuate the trap will also produce the desired longitudinal motion. Other extension systems 80, such as a spring or other elastic member located between the handle 88 and the housing 86, and other sealing systems, such as a membrane 89 that completely surrounds the handle 88, an O-ring, or a wiper style seal, are also within the scope of the present invention.

Referring again to FIG. 5 and 28, the struts 49 may be made from any elastic material. It is desirable, however, that the material be approved for use in medical devices when used in medical applications, have a relatively high modulus of elasticity, and have a relatively good resilience. One particularly desirable class of materials are "shape memory alloys," such as Nitinol®. These materials are desirable because they can be easily "taught" a shape to which they will return after having been deformed. Manufacturers can use this feature to form struts 49 that will naturally return to their arcuately expanded position when a user releases the guidewire 44. Despite these advantages, however, other strut materials are within the scope of the present invention. This specifically includes, without being limited to, stainless steel and polymers.

The guidewire 44 may be any device capable of guiding the catheter 26 into the treatment site and capable of transmitting sufficient torque from the guidewire port 34 to the struts 49. The guidewire 44 in some embodiments is made from a braided stainless steel wire. These embodiments are desirable because stainless steel has excellent strength and corrosion resistance, and is approved for use in medical devices. Stainless steel's strength and corrosion resistance may be particularly desirable for use in catheters having diameters of five French or less. Despite these advantages, non-braided guidewires 44; guidewires 44 made from other materials, such as platinum or a polymer; and embodiments having a removable guidewire 44 are within the scope of the present invention. The removable guidewire 44 in these embodiments may be operably connected to the struts 49 by any suitable means, such as mechanical or magnetic linkages.

The guidewire 44 in some embodiments may taper along its length from a larger diameter at the branching housing 28 to a smaller diameter at the trap 38. These embodiments are desirable because they help prevent the guidewire 44 and the catheter 26 from "looping" around themselves during use. Looping is commonly observed in phone cords and occurs when a wire is twisted around its longitudinal axis. Despite this advantage, non-tapered guidewires 44 are also within the scope of the present invention.

Figure 6:
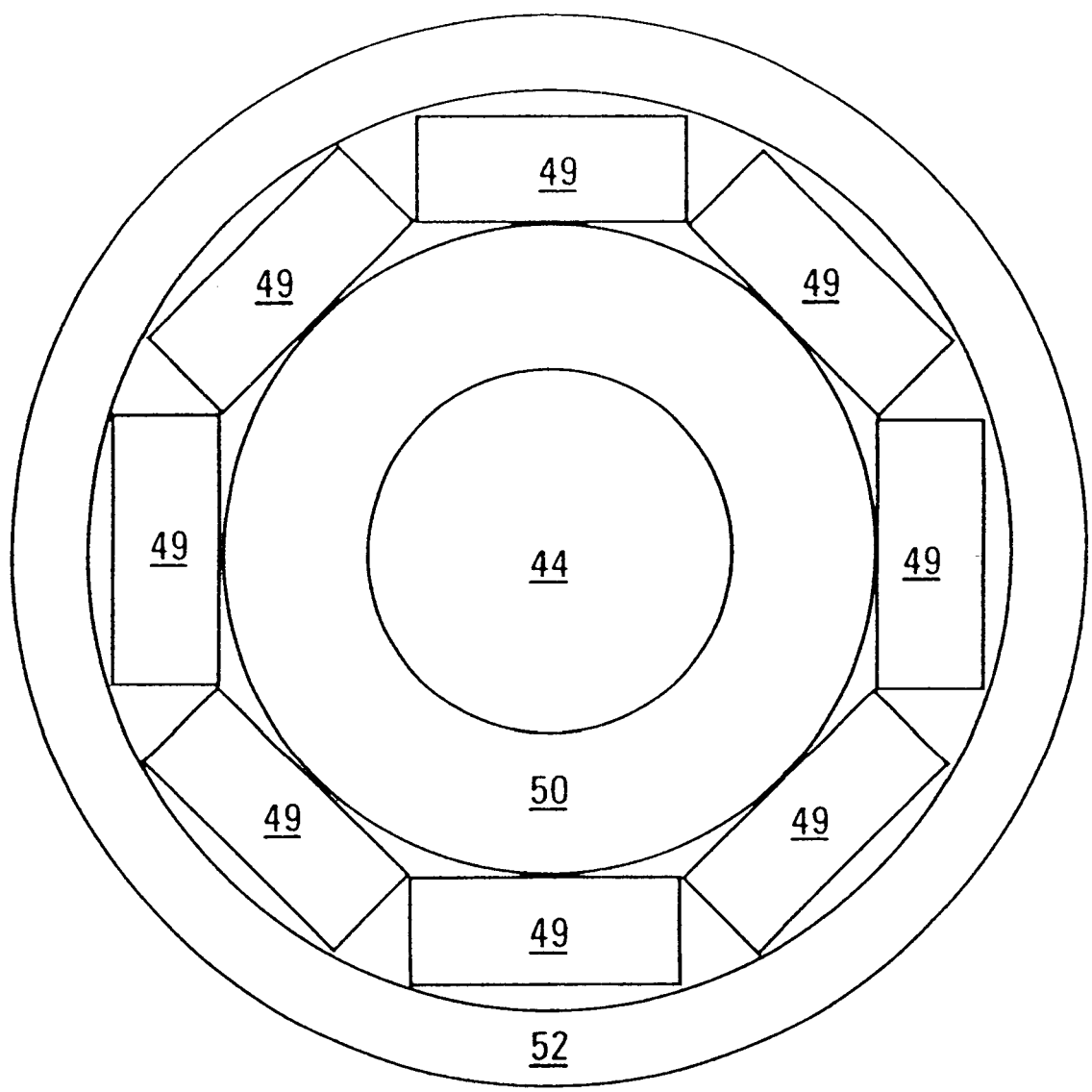
FIG. 6 is a sectional view of the embodiment depicted in FIG. 5, taken along the line CC.

In some embodiments, as best shown in FIG. 6, the struts 49 are clamped to the guidewire 44 by the rings 50 and 52. In these embodiments, the inner ring 50 is first attached to the guidewire 44 by any suitable mechanical means, such as swedging, press fitting, or brazing. The struts 49 are then aligned over the inner ring 50 and locked into place by swedging, press fitting, brazing, or other suitable means the outer ring 52 over and around the struts 49. In some embodiments, the struts 49 are coated with a material, such as textured polyurethane, that helps to prevent the struts 49 from slipping out of the rings 50 and 52 and that helps to adhesively connect the struts 49 to the membrane 56. Ring 54 similarly clamps the proximal end of the struts 49 against the inner wall 48 of the catheter 26. The single ring 54 may be attached to the struts 49 by any suitable means, such as swedging, press fitting, or through use of adhesives.

The struts 49 may also be embedded into the inner wall 48 of the catheter 26 or may be inserted into longitudinal grooves formed into the inner wall 48 in some embodiments, or alternatively, the catheter 26 may be formed or overmolded around the struts 49. These features may be desirable for small diameter angioplasty devices 20 because they may reduce the diameter of the ring 54 and because they may help to lock the struts 49 inside the ring 54. Inserting or embedding the struts 49 into the wall of the catheter can also eliminate the need for the ring 54.

Although stainless steel rings 50, 52, 54 are desirable to attach a Nitinol strut 49 to a stainless steel guidewire 44, those skilled in the art will recognize that other means of attaching the struts 49 are within the scope of the present invention. This specifically includes, without being limited to, rings 50, 52, 54 made from other materials, such as mylar, that can be bonded to the coating on the struts 49 and the use of welding and/or adhesives to directly bond the struts 49 to the guidewire 44 and/or the inner wall 48. These alternative methods may be particularly desirable when used with struts 49 that are made from materials other than Nitinol and when the guidewire 44 is made from materials other than stainless steel. These alternate attachment means may also be desirable for use with the embodiments shown in FIGS. 14–29.

The number of struts 49 and their dimensions are arbitrary. However, more struts 49 are generally desirable because they can more accurately bias the membrane 56 against the vessel or vessel-like structure. It is also desirable that each strut 49 have dimensions large enough that they can bias the membrane 56 against the vessel with sufficient force to prevent physiologically significant particles from escaping around the trap 38, but not so large that the struts 49 will prevent capture of the particles or so large that the struts 49 will interfere with each other when in their closed position. One suitable five French catheter 26 embodiment uses eight 0.006 inch×0.003 inch Nitinol struts.

The membrane 56 may be any material capable of stopping physiologically significant materials from leaving the treatment site when the trap 38 is expanded. In some embodiments, the membrane 56 is made from a relatively strong, non-elastic material. Non-elastic materials are desirable because they do not counteract the radially outward biasing force developed by the struts 49. In other embodiments, the membrane 56 is made from an elastic or semi-elastic material, such as polyurethane, polyester, polyvinyl chloride, or polystyrene. These embodiments are desirable because the elasticity may help the struts 49 to close the trap 38. In still other embodiments, the membrane 56 is porous. These embodiments may be desirable because the pressure developed by patient's heart will help deliver particles into the trap 38.

FIG. 11A shows an angioplasty device 20 capable of providing suction distal to the angioplasty device 20 while it is being inserted into the treatment site. In this embodiment, the ring 50 is replaced with a disk 92 attached to the inner wall 48 and a disk 94 attached to the guidewire 44. These two disks 92 and 94 act as a valve capable of selectively permitting suction to that portion 99 of the vessel immediately in front of the angioplasty device 20. That is, as shown in FIGS. 11B and 11C, each disk 92 and 94 has two open portions 96 and two blocking portions 98. Rotation of the guidewire 44 causes disk 94 to rotate relative to disk 92. This relative motion causes the disks 92 and 94 to alternate between an "open" orientation in which the openings 96 in disk 92 are aligned with the openings 96 in disk 94 and a "closed" orientation in which the openings 96 in disk 92 are aligned with the blocking portions 98 in disk 94. Preferably, the same rotation of the guidewire 44 used to toggle the disks 92 and 94 between their open and closed orientations also expands and contracts the trap 38.

In operation, the user would first rotate the guidewire 44 until the disks 92 and 94 are in the open orientation. In this orientation, the openings 96 cooperate to create a fluid communication channel between the suction lumen 42 and that portion 99 of the vessel immediately distal to the angioplasty device 20. This allows the user to provide suction in front of the angioplasty device 20 while the user inserts it into the vessel. Once the angioplasty device 20 is in place, the user will rotate the guidewire 44 until the disks are in the closed orientation. In this orientation, the blocking portions 98 cooperate to prevent fluid from flowing through the disks 92 and 94. This, in turn, creates suction inside the trap 38.

FIGS. 12A and 12B show an angioplasty device 20 with an alternate valve embodiment 120. This valve embodiment 120 comprises a disk shaped abutment 121 that is rigidly attached to the catheter wall 48 and a stopper 122 that is rigidly attached to the guidewire 44 at a location distal to the abutment 121. The stopper 122 has a conically shaped surface 124 on its distal end and a generally planar engagement surface 126 on its proximal end. The engagement surface 126 of the stopper 122 can selectively plug a circular flow channel 128 that is coaxially located in the abutment 121. The valve 120 allows the user to apply suction to the portion 99 of the vessel immediately in front of the angioplasty device 20 through a hole 129 in the membrane 56.

In operation, the valve embodiment 120 is actuated by longitudinally moving the guidewire 44 relative to the catheter wall 48. That is, pulling the guidewire 44 in a proximal direction relative to the catheter wall 48 causes the generally planar engagement surface 126 to sealably engage the abutment 121, which prevents fluid from flowing through the circular flow channel 128. Pushing the guidewire 44 in a distal direction relative to the catheter wall 48 causes the stopper 122 to disengage from the abutment 121, which allows fluid to flow through the circular flow channel 128.

Other valve embodiments 120 capable of being actuated by longitudinal motion are also within the scope of the present invention. For example, the stopper 122 may be rotated 180 degrees so that the conically shaped surface 124 engages the abutment 121, rather than the generally planar engagement surface 126. These embodiments may be desirable because the conically shaped surface 124 will self-center the stopper 122 in the flow channel 128. Also, the stopper 122 may be located proximal to the abutment 121. In addition, the stopper 122 may have other shapes, such as a sphere or a cylinder.

Those skilled in the art will recognize that the valve, 120 and the disks 92, 94 can be eliminated in these embodiments, which allows the suction lumen 42 to simultaneously provide suction under the trap 38 and distal to the angioplasty device.

Figure 13:
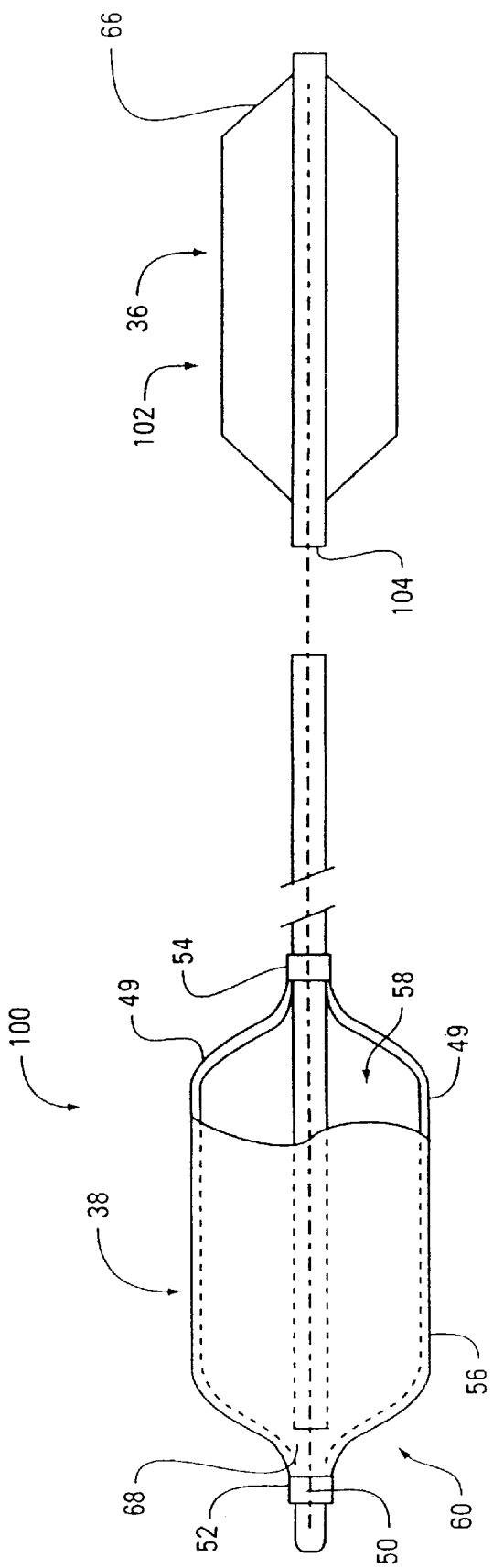
FIG. 13 is a side plan view of an embodiment having separate catheters for the trap and the operative member.

FIG. 13 shows an embodiment where the balloon 36 and the trap 38 are associated with separate catheter bundles. That is, FIG. 13 shows an embodiment of the present invention comprising a trap catheter bundle 100 for the trap 38 and a balloon catheter bundle 102 for the balloon. In operation, the trap catheter bundle 100 is inserted into vessel until the trap 38 is situated distal to the obstruction site. The balloon catheter bundle 102 is then loaded over the trap catheter bundle 100 and used to remove the obstruction. This balloon catheter bundle 102 should have a centrally located lumen 104 having an interior diameter larger than the trap catheter bundle 100. Alternatively, the balloon catheter bundle 102 or other device (such as an angioscope) may be delivered to the treatment area through a lumen 150 and an opening 152 in the trap catheter bundle 100 (see FIGS. 16–18).

Figure 14:
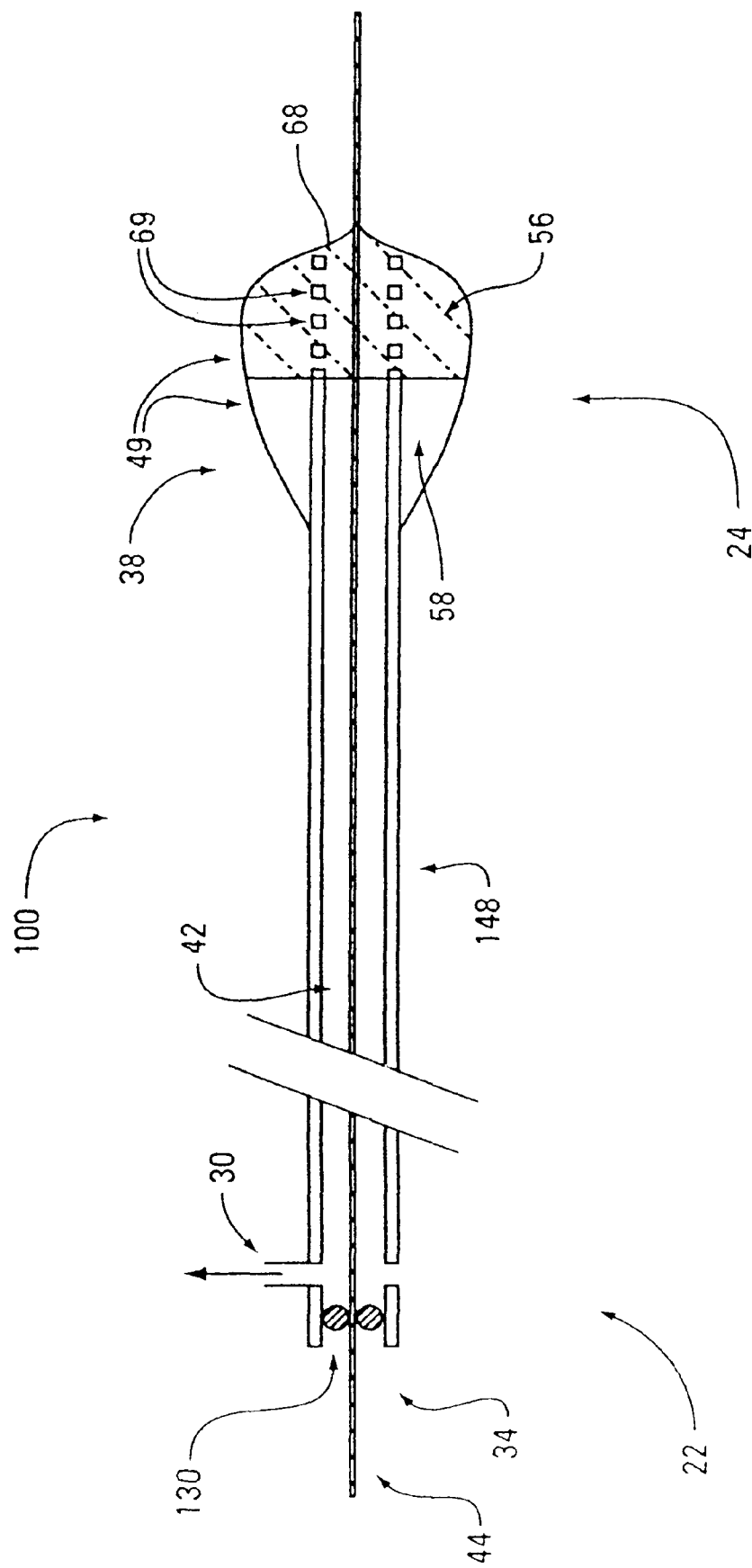
FIG. 14 is a sectional view of a trap catheter bundle embodiment configured for use in the antegrade direction.
Figure 15:
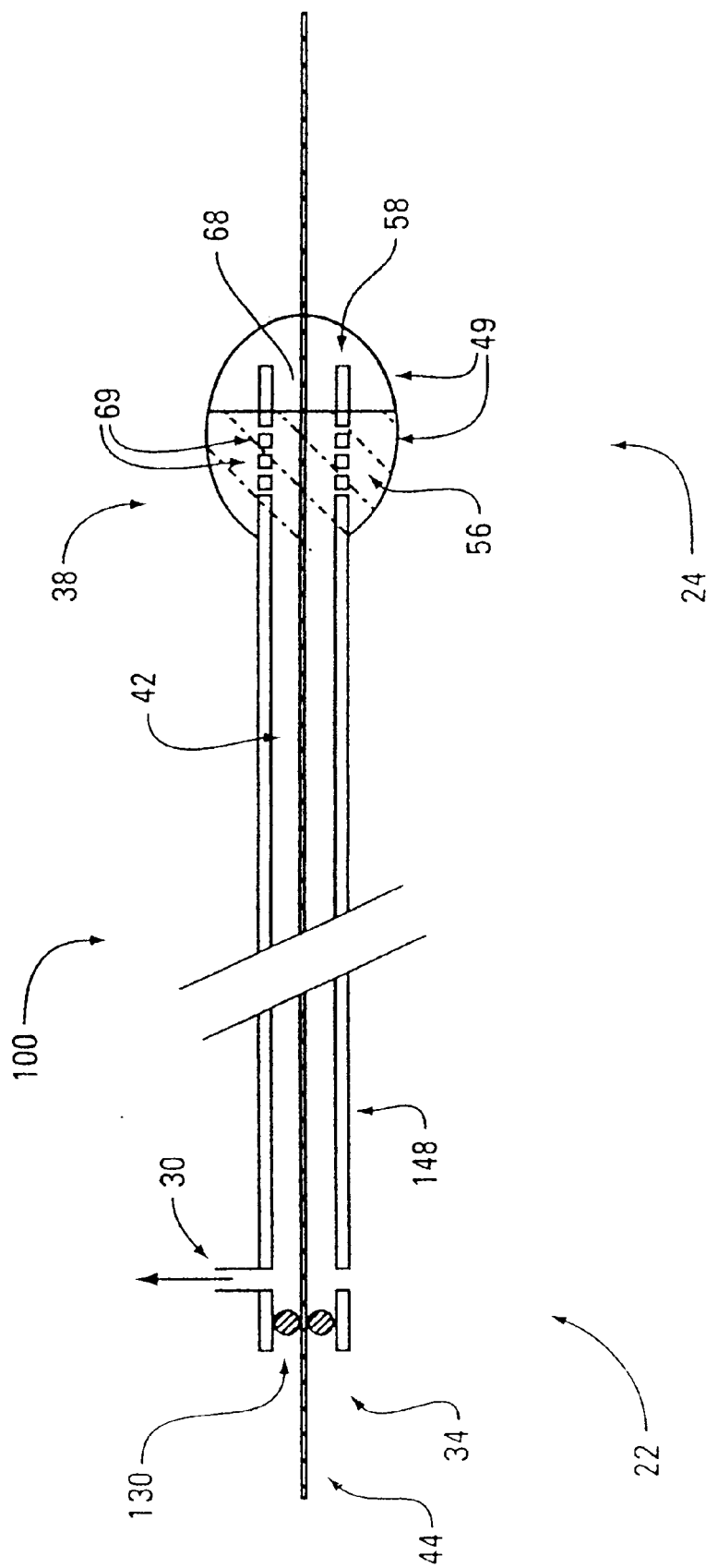
FIG. 15 is a sectional view of a trap catheter bundle embodiment configured for use in the retrograde direction.

FIGS. 14 and 15 are sectional views of two trap catheter bundle embodiments 100. Specifically, the trap catheter bundle 100 in FIG. 14 is configured to be inserted in an antegrade direction (i.e., in same the direction as the fluid flow) along a guidewire 44. Thus, the opening 58 in its membrane 38 faces towards its proximal end. The opening 58 in FIG. 15, in contrast, faces the catheter's distal end because this catheter bundle 100 is configured to be inserted in a retrograde direction (i.e., with insertion site "downstream" in relation to the direction of fluid flow) along a guidewire 44. Both trap catheter bundles 100 may be sized and shaped so that they can be inserted through the guidewire channel of a balloon catheter bundle 102. Those skilled in the art will recognize that the trap catheter bundle embodiments 100 in FIGS. 14 and 15 can also be used to capture embolic debris without a balloon catheter bundle 102 and to deliver diagnostic and therapeutic agents to a treatment area.

FIGS. 14 and 15 also show a seal 130 that may be used in place of or in addition to the flexible membrane extension system 80a depicted in FIG. 10 to prevent air or other fluid from leaking into the suction lumen 42. Accordingly, the seal 130 may be any device, such as an elastomeric O-ring or wiper, that prevents fluid from leaking through the guidewire port 34 and that allows the guidewire 44 to move relative to the catheter wall 148. Embodiments using an O-ring or a wiper style seal 130 are particularly desirable because the user can slide the guidewire 44 longitudinally relative to the catheter bundle 102 to help actuate the trap 38.

Figure 16:
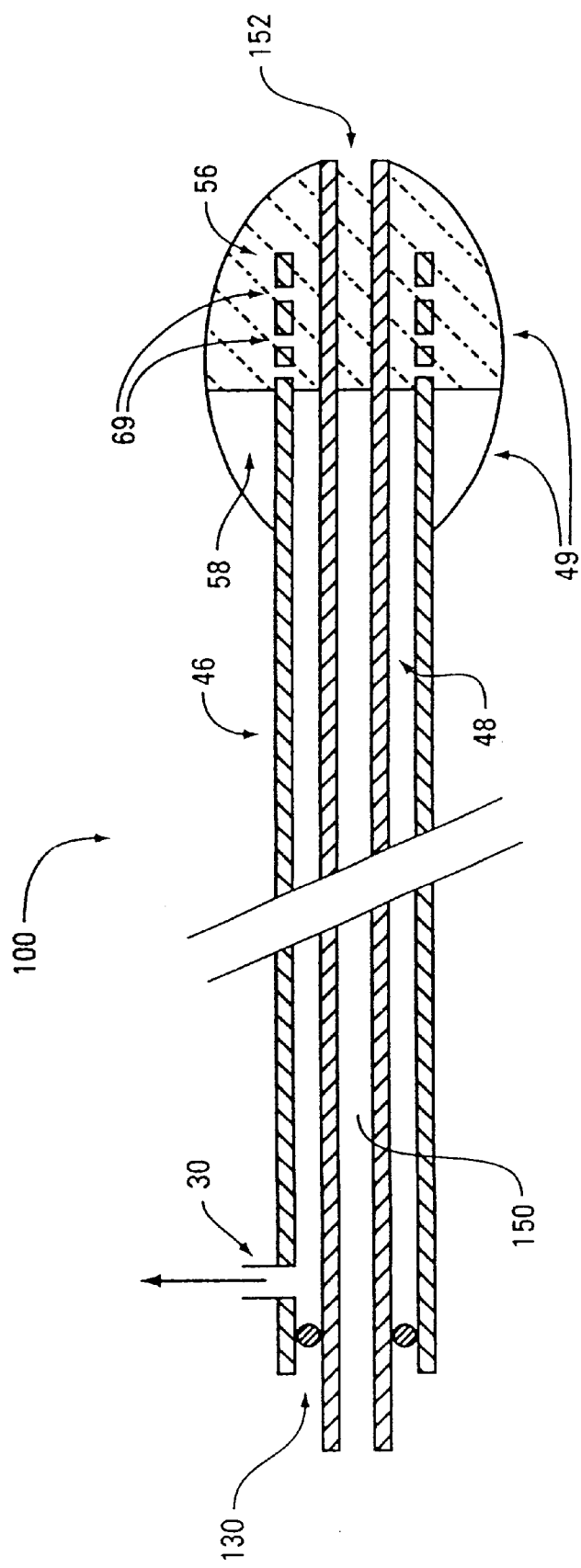
FIG. 16 is a sectional view of a trap catheter bundle embodiment configured for use in the antegrade direction, in which the trap is actuated by relative motion between an inner catheter wall and an outer catheter wall.
Figure 17:
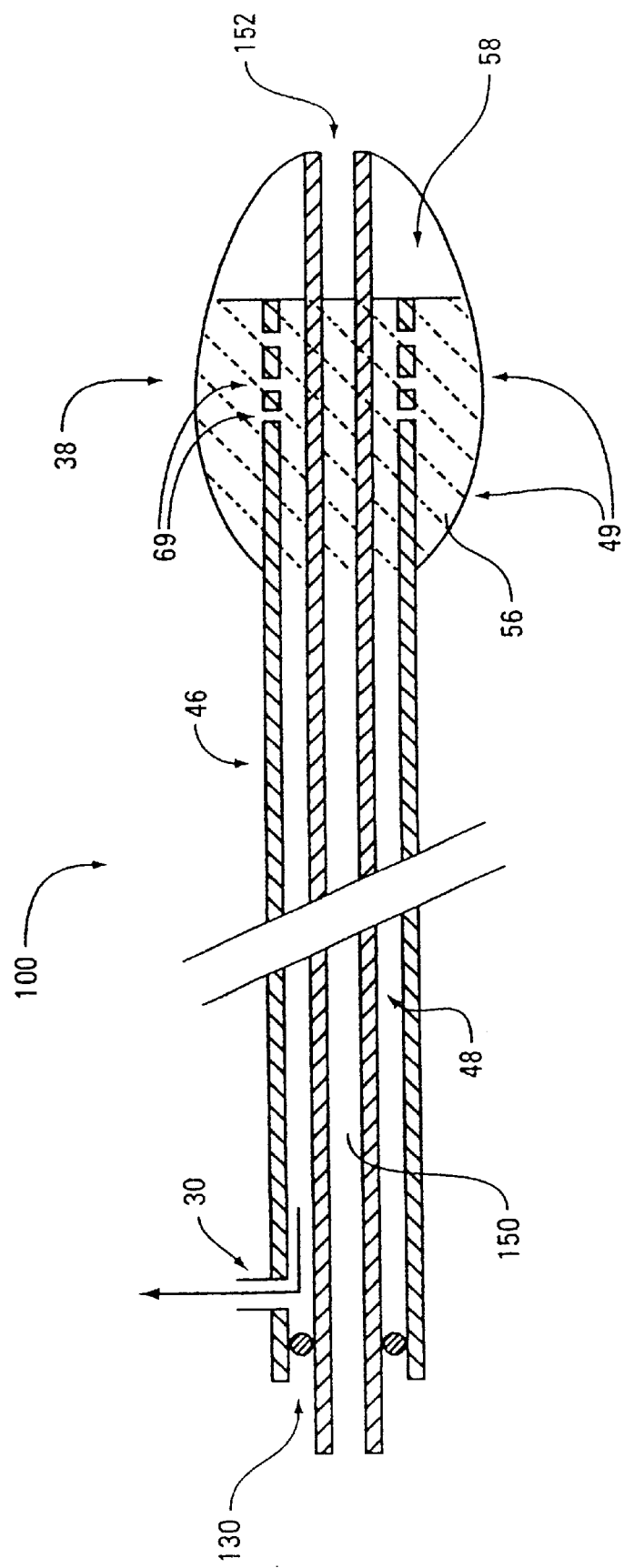
FIG. 17 is a sectional view of a trap catheter bundle embodiment configured for use in the retrograde direction, in which the trap is actuated by relative motion between an inner catheter wall and an outer catheter wall.

FIGS. 16 and 17 are sectional views of two trap catheter bundle embodiments 100 in which the trap is actuated by relative motion between the inner catheter wall 48 and the outer catheter wall 46. That is, the user actuates the trap 38 in this embodiment by rotating the inner catheter wall 48 relative to the outer catheter wall 46, rather than rotating a fixed guidewire 44 relative to the inner catheter wall 48. These embodiments are desirable because they can be loaded over a separate guidewire (not shown) or angioplasty device (not shown) that has previously been inserted into the patient using lumen 150 and opening 152. These embodiments are also desirable because inner catheter wall 48 can be slid longitudinally with respect to the outer catheter wall 46 to help open and close the trap 38. In an appropriately designed balloon catheter bundle, these trap catheter bundles could be inserted through the lumen 150 of the angioplasty balloon catheter. Like the trap catheter bundle embodiments 100 in FIGS. 14 and 15, the trap catheter embodiments 100 in FIGS. 16 and 17 can be inserted in either the antegrade or retrograde direction, and can be used with or without a separate balloon catheter bundle 102.

Figure 1:
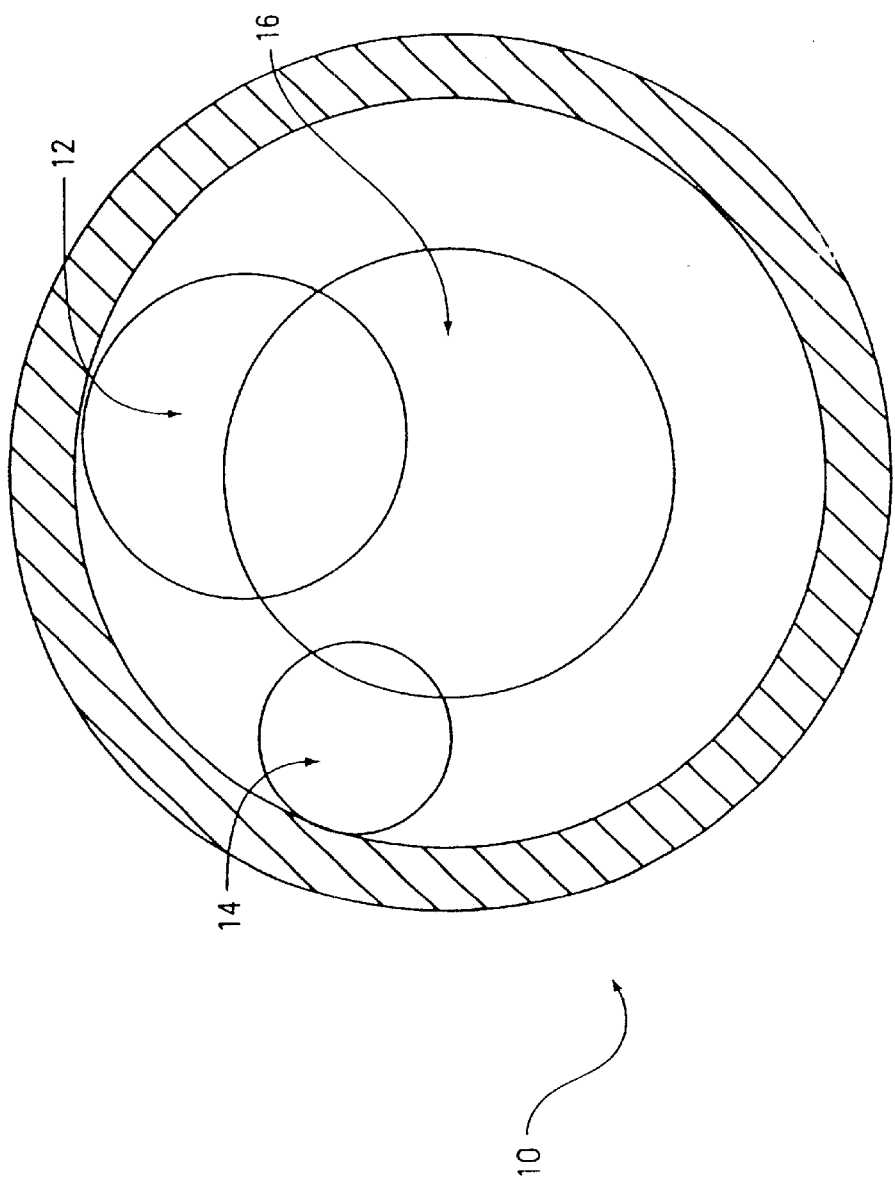
FIG. 1 (prior art) is a sectional view illustrating the size limits of a conventional five French catheter.
Figure 18:
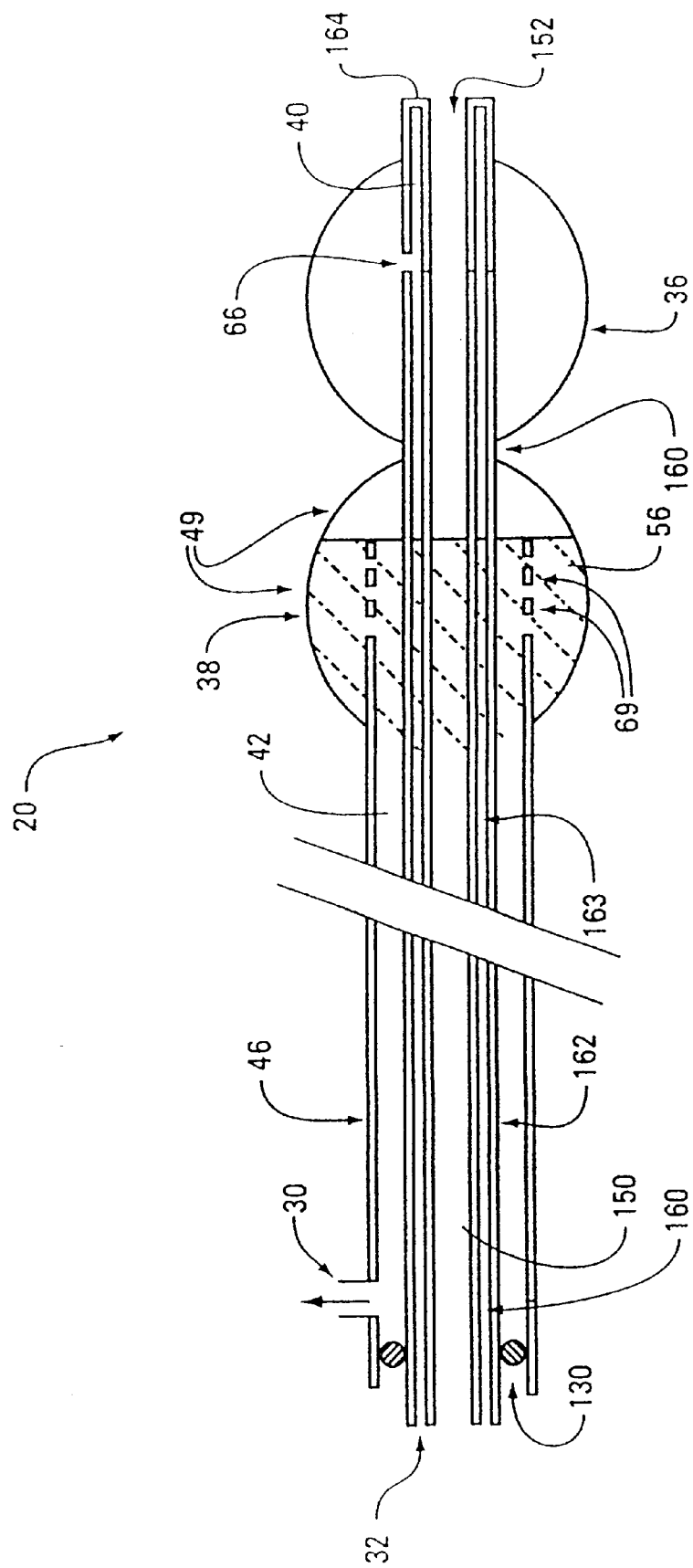
FIG. 18 is a sectional view of an angioplasty device embodiment configured for use in the retrograde direction in which the trap is actuated by relative motion between an inner catheter wall and an outer catheter wall.

FIG. 18 is a sectional view of an angioplasty device 20 embodiment for use in retrograde applications (see FIG. 1 of U.S. Pat. No. 4,794,928 for conceptional orientation, which is herein incorporated by reference). This embodiment comprises a separate catheter 160 for the balloon 36 and for the inflation/deflation lumen 40. This catheter 160 has a first wall 162, a second wall 163, and an end wall or plug 164. In operation, the trap 38 in this embodiment is actuated by relative rotational and/or longitudinal motion between the exterior wall 46 and the first wall 162 of the catheter 160. Like the embodiments in FIGS. 14–17, this angioplasty device embodiment 20 can be loaded over a separate guidewire (not shown) or catheter (not shown) that has previously been inserted into the patient using lumen 150 and opening 152. Also like the embodiments in FIGS. 14–17, the trap 38 in this embodiment can be actuated using relative rotational motion or a combination of relative longitudinal and relative rotational motion.

Figure 19:
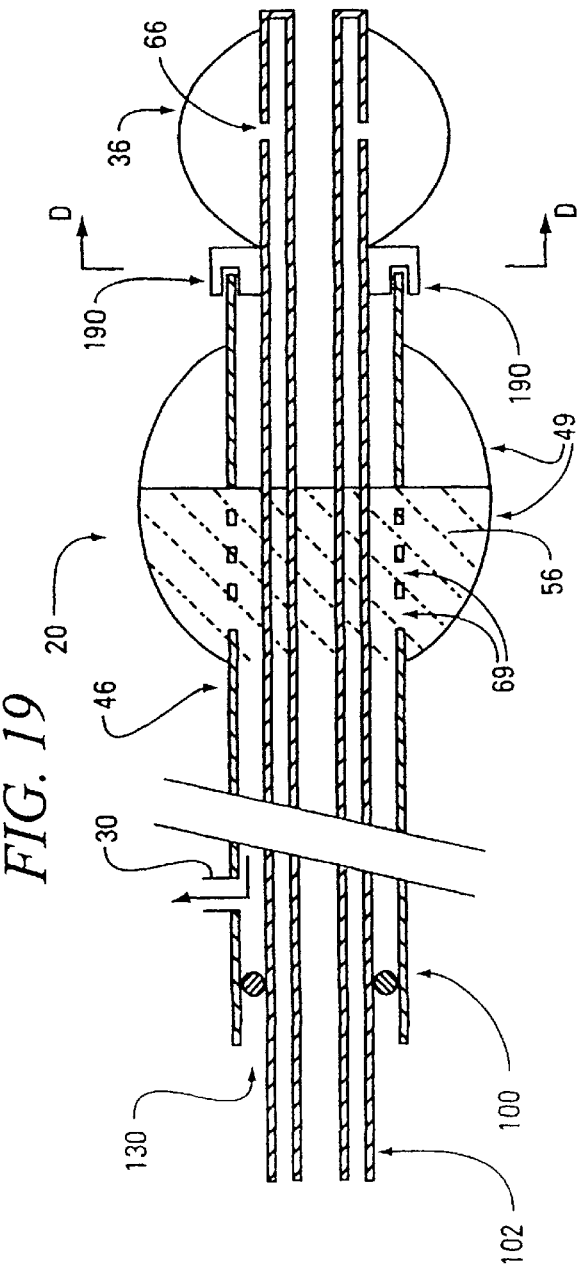
FIG. 19 is a sectional view of an angioplasty device embodiment having a coupling device.
Figure 20:
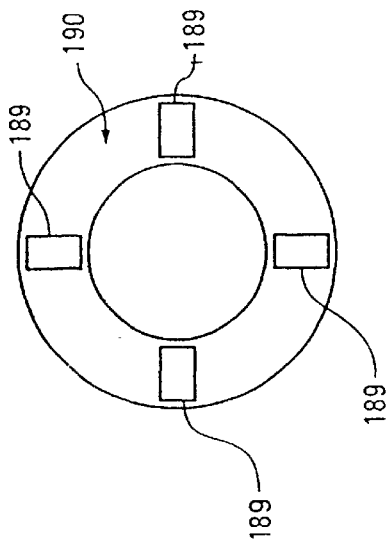
FIG. 20 is a sectional view of the coupling device in FIG. 19.
Figure 27:
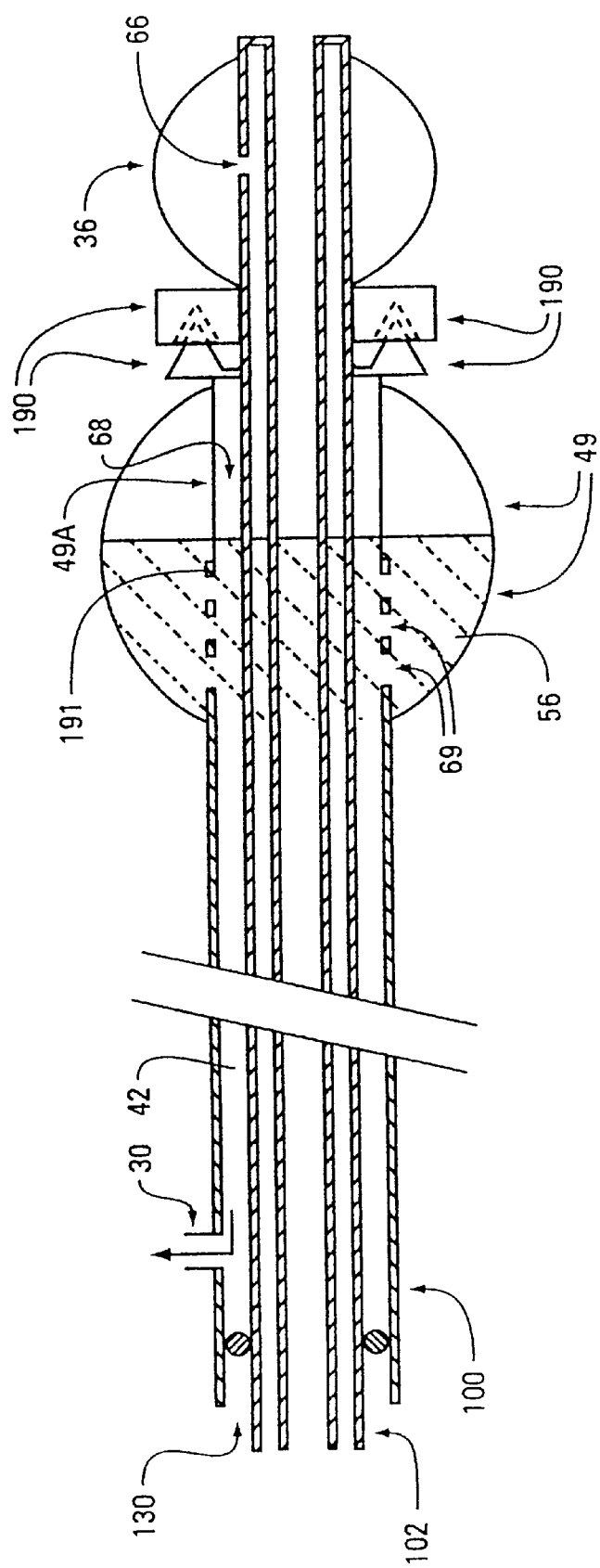
FIG. 27 is a sectional view of an embodiment in which a plurality of struts connect a coupling device to the angioplasty catheter.

FIG. 19 is a sectional view of an angioplasty device embodiment having a coupling device 190 with four radially spaced sockets 189. FIG. 20 is a sectional view of the coupling device 190. The coupling device 190 in this embodiment may be any device that prevents the balloon catheter 102 from rotating relative to the trap catheter bundle 100 (or translating, if used with the trap embodiment 38 described with reference to FIGS. 21 and 22). These embodiments are desirable because the trap catheter bundle 100 and the balloon catheter bundle 102 may be manufactured separately, then combined as needed. FIG. 27 depicts an alternate embodiment in which a second group of struts 49*a* connect the coupling device 190 to an end 191 of the trap catheter bundle 100. In operation, the trap catheter bundles 100 in FIGS. 19 and 27 may be inserted over an in-place balloon catheter 102 and then either removed along with the balloon catheter 102 or by itself, depending on the configuration of the coupling devices 190. The embodiments in FIGS. 19 and 27 may also be inserted over a guidewire 44 (not shown) or a may have a fixed guidewire 44 extending distally from it.

FIGS. 21 and 22 are sectional views of another trap catheter bundle embodiment 100, in which the trap 38 is actuated by a translation between the guidewire 44 and the catheter wall 148. In this embodiment, a first end 180 of the struts 49 is connected to the guidewire 44 and a second end 182 of the struts 49 is attached to the catheter wall 148. Translating the guidewire 44 (i.e., moving the guidewire in an axial direction) relative to the catheter wall 148 biases the first end 180 away from the end 182. This, in turn, actuates the struts 49 between an arcuately expanded position, such as that shown in FIG. 21, and a contracted position, such as that shown in FIG. 22. Accordingly, the struts 49 in this embodiment remain generally parallel to the guidewire 44 throughout the procedure. Those skilled in the art will recognize that this actuation mechanism also could be used with the embodiments described with reference to FIGS. 1–20.

Figure 23A:
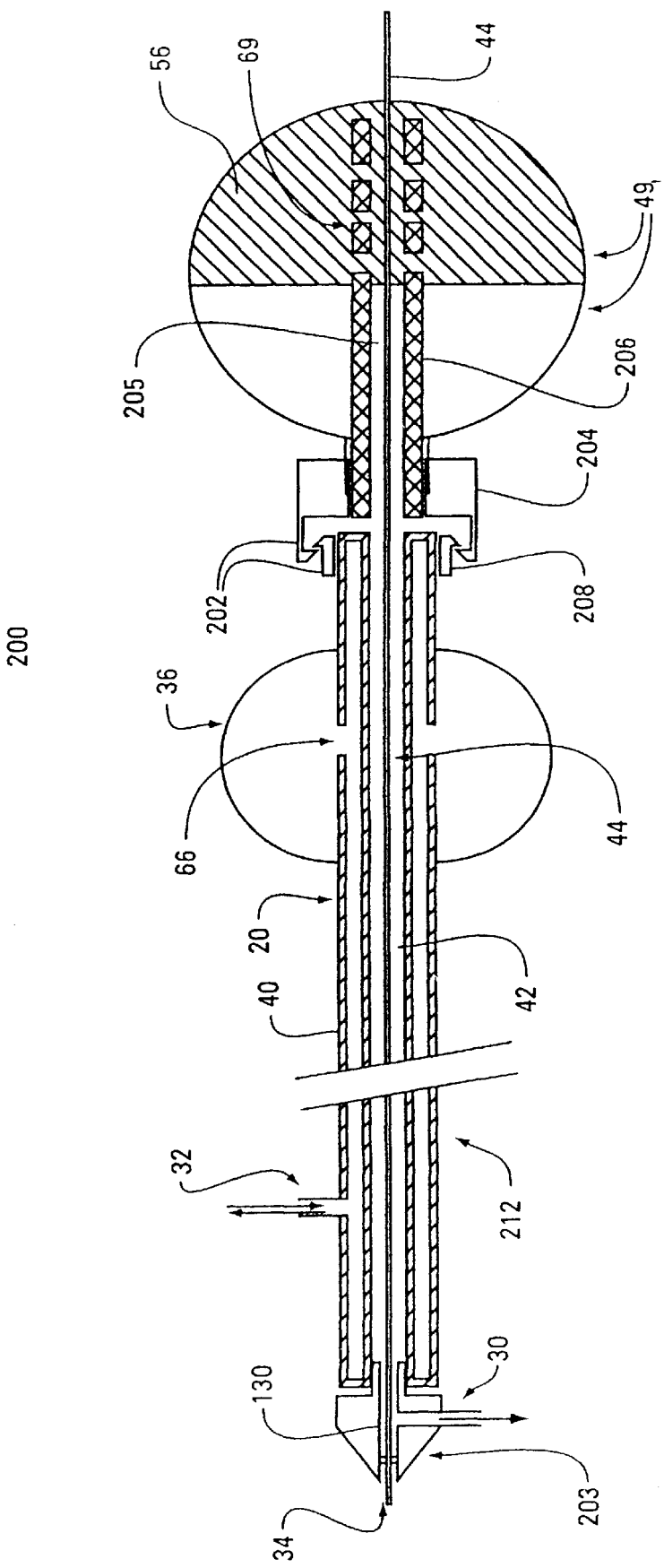
FIGS. 23A is a sectional view of a modular trap embodiment.

FIGS. 23A–24B are sectional views of two modular trap embodiments 200 having an adaptive coupling device 202, and a permanent or detachable and/or insertable manifold 203. These embodiments are desirable because the user can add aspiration and blocking features to a conventional angioplasty device 212. In FIG. 23A, the coupling device 202 comprises a male snap ring 204 that is adhesively bonded to a modular catheter wall 206 and a female snap ring 208 that is adhesively bonded to an outer wall 210 of a conventional angioplasty device 212. The snap rings 204 and 208 sealably mate together, which fluidly connects a modular catheter lumen 205 to the suction lumen 42. In FIG. 24A, the coupling device 202 comprises a first ring 220 and a second ring 222. The first ring 220 has a circumferential slot 224 in its proximal end into which the struts 49 are fixed and a circumferential tab 226 that projects axially from its distal end. The second ring 222, which is attached to a conventional angioplasty device 212, has a circumferential slot 228 into which the tab 226 is press fit, snap fit, or otherwise locked shortly before use. Alternatively, the second ring 222 could be eliminated and the tab 226 inserted directly into, and held in place by, the suction lumen 42 and/or an adhesive or tape. The embodiment in FIG. 24A may be particularly desirable because it does not require a modular catheter wall 206.

Figure 23B:
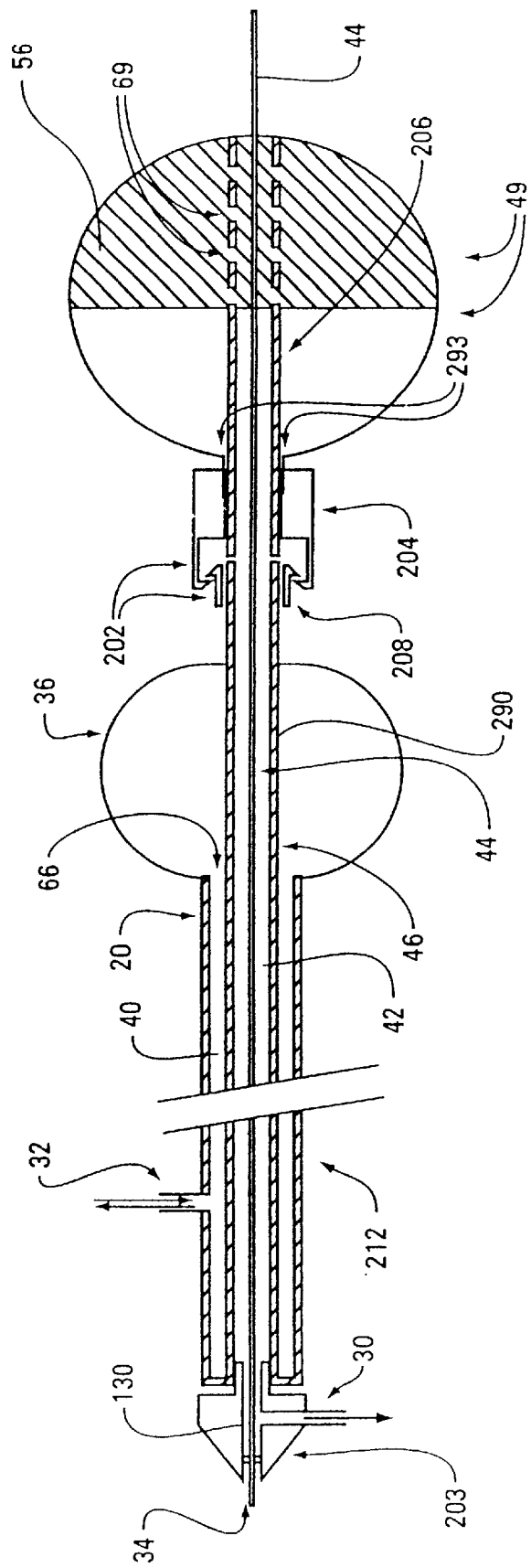
FIGS. 23B, 24A, and 24B are sectional views of alternate modular trap embodiments.
Figure 24A:
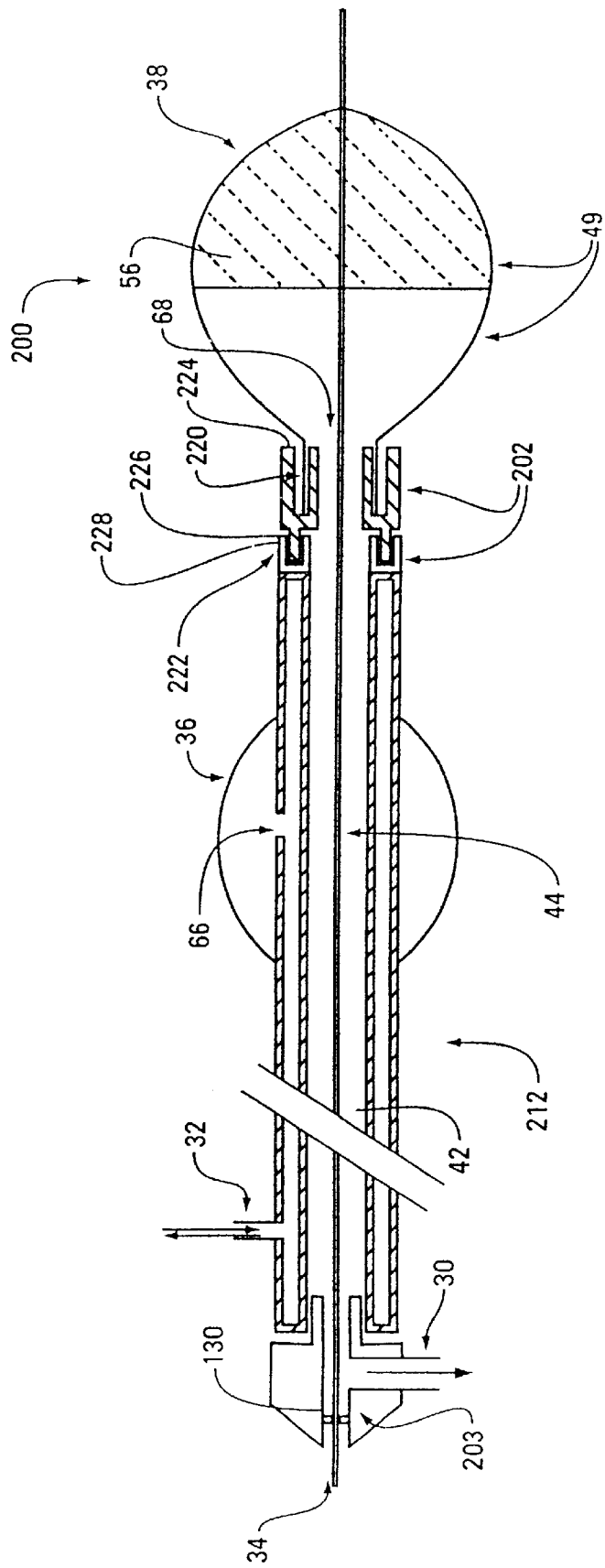
Figure 24B:
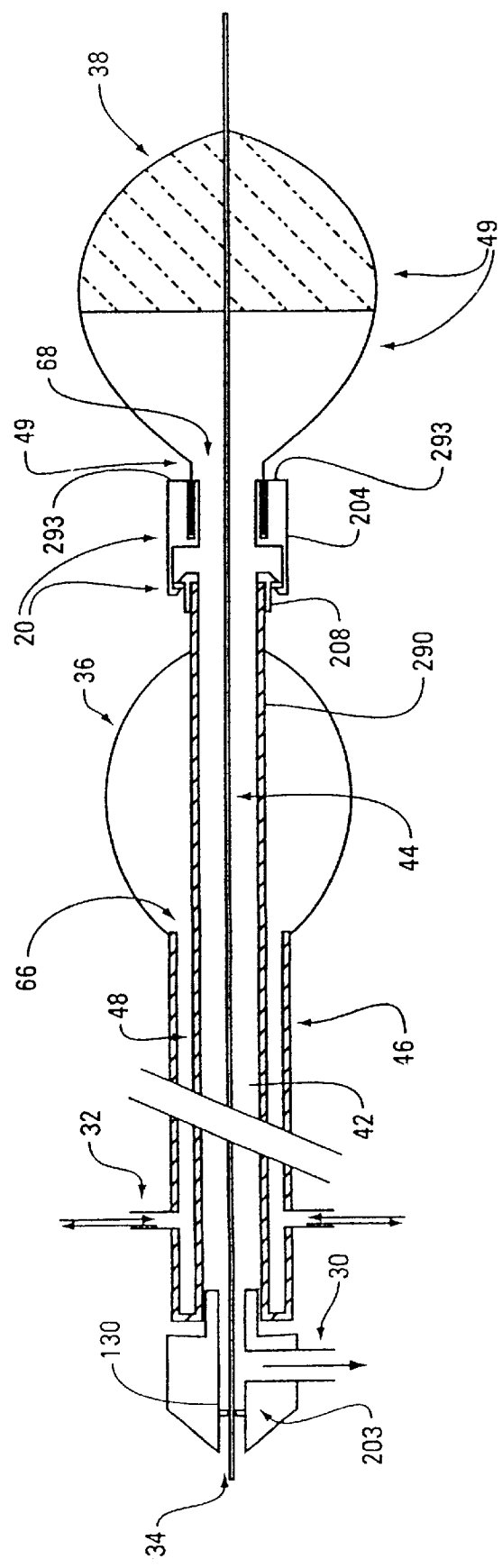

Alternately, as shown in FIGS. 23B and 24B, the snap ring 208 (or the second ring 222) could also be attached to the inner wall 48. These embodiments may be desirable because they provide a lower profile balloon catheter. FIGS. 23B and 24B also show that the snap ring 204 can have a circumferential slot 293 in its proximal end into which the struts 49 are fixed.

Figure 25:
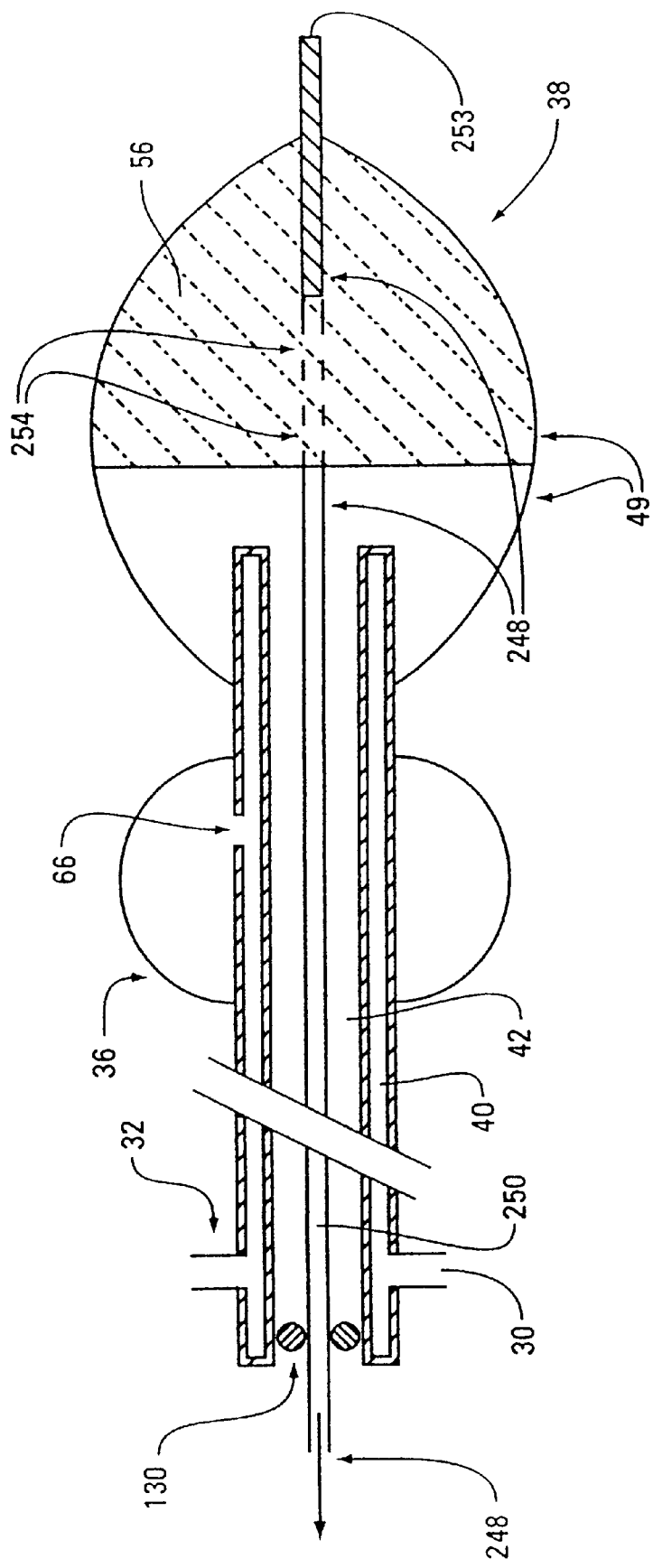
FIG. 25 is a sectional view of an embodiment having a hollow guidewire.
Figure 26:
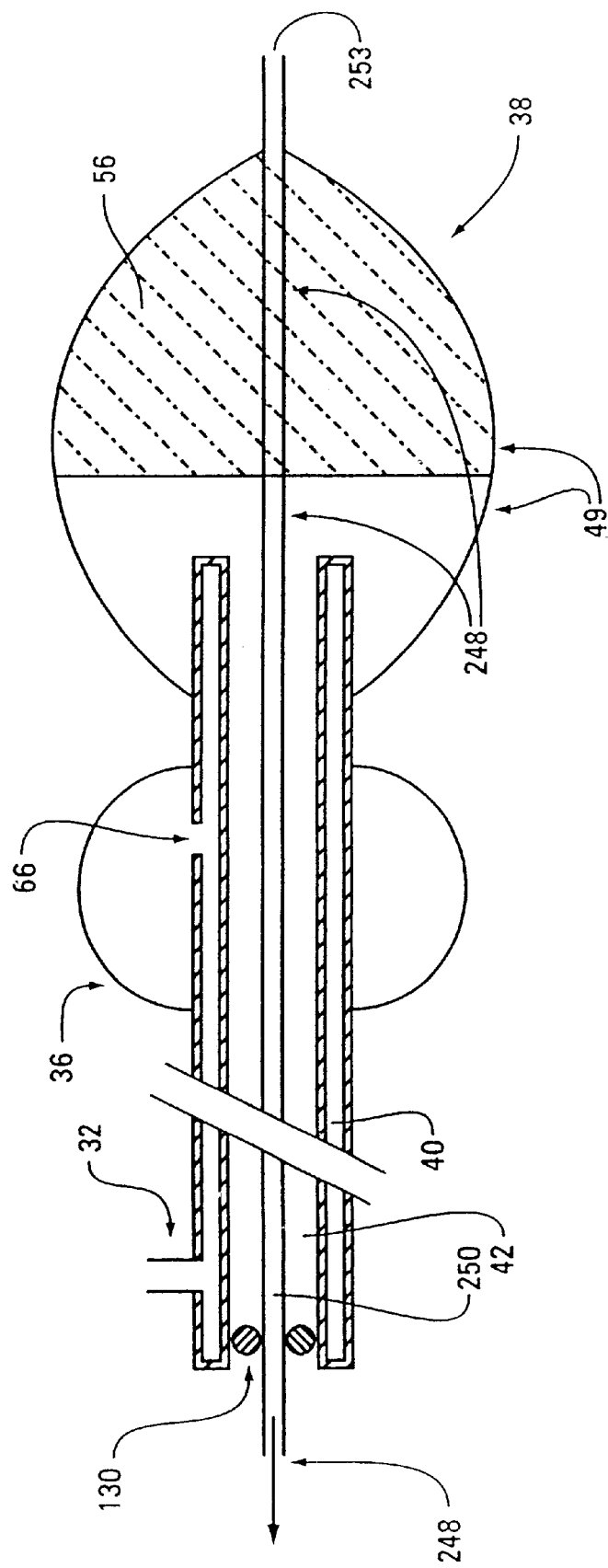
FIG. 26 is a sectional view of an alternate embodiment having a hollow guidewire.

FIGS. 25 and 26 are sectional views of two embodiments having a hollow guidewire 248. These embodiments are desirable because a lumen 250 defined by the hollow guidewire 248 can be used as an alternate suction lumen. The hollow guidewire 248 in these embodiments includes a single opening 253 and/or a plurality of pores 254 that are radially and axially spaced inside the struts 49. The pores 254 allow the alternate suction lumen 250 to help the suction lumen 42 remove smaller particles from the treatment site and suck larger particles into the trap 38. The opening 253 allows the alternate suction lumen 250 to selectively provide suction distal to the angioplasty device 20 while it is being inserted into the treatment site and allows the alternate suction lumen 250 to selectively deliver treatment and/or diagnostic agents. Those skilled in the art will recognize that the hollow guidewire 248 may also be used in the embodiments described with reference to FIGS. 2–24B and 27–28 and that the housing 28 can be modified to include two or more suction ports.

Referring again to FIG. 2, the guidewire port 34 can be any device that allows for relative rotation of the guidewire 44 with respect to the catheter 26. In some embodiments, the guidewire port 34 may include an apparatus (not shown) that will indicate the relative position and/or torque of the guidewire with respect to the catheter 26. These embodiments may be desirable because they can help ensure that the struts 49 are rotated into their fully expanded position. The guidewire port 34 may include an auxiliary apparatus (not shown) that maintains the guidewire 44 in a particular orientation corresponding to the maximum expanded position. This apparatus may reduce the number of medical personnel necessary to perform the entire procedure.

The suction port 30 and the inflation port 32 may be any devices that, respectively, allow for operable connection to a vacuum source and a pressure source. In some embodiments, the suction port 30 and the inflation port 32 comprise a polymeric tube that is adapted to receive to a syringe. One syringe may contain the fluid to be injected through the inflation/deflation lumen 40 and into the balloon 36. Another syringe may suck fluid and particles from the trap 38 through the suction lumen 42.

The present invention offers many advantages over the known angioplasty devices. For example, it provides a total capture angioplasty device that can be scaled into small diameter devices. Total capture angioplasty devices having dimensions of about five French and smaller can be easily achieved with the present invention. The present invention can also provide a fixed guidewire to aid insertion into irregular stenosis and a trap 38 that may be actively closed around particles that are too large to be sucked through the suction lumen 42. In addition, the struts 49 can act as an additional trap during actuation. That is, as the trap 38 is contracted, the struts 49 prevent smaller and smaller particles from escaping. In addition, the present invention maximizes the amount and rate of suction per unit size.

Although the present invention has been described in detail with reference to certain embodiments thereof, it may be embodied in other specific forms without departing from the essential spirit or attributes thereof. For example, lumens 42 and 150 could be used to introduce medicinal agents and radiopaque liquids, or to take samples of a fluid before, during, or on completion of a procedure. In these embodiments, the medicinal agent could be introduced into the catheter 26 through an appropriate port by suitable means, such as a syringe. These embodiments may be particularly desirable if combined with a porous membrane 56. In addition, the stainless steel guidewire 44 could be replaced by an optical fiber. These embodiments may be desirable because they could allow the surgeon to view the treatment site before and after the procedure. Still other embodiments of the present invention may coat the guidewire 44 and the catheter 26 with a lubricant, such as polytetrafluoroethylene ("PTFE"), to reduce friction.

Those skilled in the art will recognize that the term "angioplasty" as used throughout this specification and the claims was intended to include, without being limited to: (1) any of the medical and/or veterinary procedures and treatments described in the background section; (2) procedures and treatments similar to those described in the background section; and/or (3) any other treatment or procedure involving the removal of an obstruction from vessels or vessel-like structures, regardless of whether such structures are part of or associated with a living organism, and specifically including, without being limited to, the use of the present invention to remove obstructions from "non-living" tubes, tubules, conduits, fibers or other structures in non-medical or industrial applications. Thus, the present invention could, for example, be used to remove an obstruction from a fluid delivery tube within a machine under conditions where it would be undesirable for particles of the obstruction to break free and continue down the tube, e.g., if the machine were still running and particles would jeopardize continued operation.

Those skilled in the art will also recognize that the accompanying figures and this description depict and describe embodiments of the present invention, and features and components thereof. With regard to means for fastening, mounting, attaching or connecting the components of the present invention to form the mechanism as a whole, unless specifically described otherwise, such means were intended to encompass conventional fasteners such as machine screws, nut and bolt connectors, machine threaded connectors, snap rings, screw clamps, rivets, nuts and bolts, toggles, pins and the like. Components may also be connected by welding, brazing, friction fitting, adhesives, or deformation, if appropriate. Electrical connections or position sensing components may be made using appropriate electrical components and connection methods, including conventional components and connectors. Unless specifically otherwise disclosed or taught, materials for making components of the present invention were selected from appropriate materials, such as metal, metallic alloys, fibers, polymers and the like, and appropriate manufacturing or production methods including casting, extruding, molding and machining may be used. In addition, any references to front and back, right and left, top and bottom and upper and lower were intended for convenience of description, not to limit the present invention or its components to any one positional or spatial orientation. Therefore, it is desired that the embodiments described herein be considered in all respects as illustrative, not restrictive, and that reference be made to the appended claims for determining the scope of the invention.

I claim:

1. A device for capturing particles flowing through a vessel or vessel like-structure, the device comprising:
    a catheter for insertion into the vessel, the catheter having a suction lumen;
    a plurality of flexible struts having a first end connected to the catheter and a second end connected to a guidewire, the struts having a contracted position wherein the struts are helically twisted around the catheter and an expanded position wherein the struts extend arcuately outward from the catheter;
    a membrane connected to the plurality of flexible struts to define a trap; and
    an actuation mechanism coupling the guidewire to the catheter for causing a combined rotation and longitudinal motion of the guidewire wherein the suction lumen has a distal aperture and at least one suction aperture located on a peripheral wall thereof, the apertures being located within the trap to allow removal of material therein.

2. The device of claim 1 further comprising an operative member coupled to the catheter, the operative member adapted to remove or compress an obstruction in the vessel.

3. The device of claim 2 wherein the operative member is a balloon and further wherein the catheter includes an inflation lumen in operable communication with the balloon.

4. The device of claim 3 wherein the inflation lumen terminates at an opening located near a proximal end of the balloon.

5. The device of claim 2 wherein the operative member is a second catheter with a balloon, the second catheter adapted for insertion into the vessel over the catheter.

6. The device of claim 3 wherein the suction lumen and the inflation lumen are disposed coaxially within the catheter.

7. The device of claim 1 wherein the plurality of struts are constructed from Nitinol.

8. The device of claim 7 wherein the plurality of struts are biased toward the expanded position.

9. The device of claim 1 wherein the vessel is a human blood vessel.

10. The device of claim 1 wherein the catheter has a diameter of about five French or less.

11. The device of claim 1 wherein the actuation mechanism is a screw extension system wherein the ratio between the rotation and the longitudinal motion of the guidewire is controlled by a pitch of the screw extension system.

12. The device of claim 1 wherein the actuation mechanism is a flexible membrane connected between the guidewire and the catheter, such that rotation of the guidewire causes a corresponding longitudinal motion of the guidewire.

13. The device of claim 1 wherein, in the contracted position, the longitudinal distance between the first and second ends of the struts is greater than the longitudinal distance between the first and second ends of the struts in the expanded position.

14. The device of claim 1 wherein the membrane is impermeable.

15. A device for capturing particles flowing through a vessel, the device comprising:
    a catheter for insertion into the vessel, the catheter having a longitudinal lumen therein;

a plurality of flexible struts having a first end connected to the catheter and a second end connected to a moveable member, the struts having a contracted position wherein the struts are helically twisted around the catheter and an expanded position wherein the struts extend arcuately outward from the catheter; and a membrane connected to the plurality of flexible struts to define a trap;

wherein, in the contracted position, a longitudinal distance between the first and second ends of the struts is greater than the longitudinal distance in the expanded position wherein the longitudinal lumen has a distal aperture and at least one suction aperture located on a peripheral wall thereof, the apertures are being located within the trap to allow removal of material therein.

16. The device of claim 15 wherein the moveable member is a guidewire.

17. The device of claim 15 wherein the moveable member is a second catheter adapted to fit within the lumen of the catheter, the second catheter having a second longitudinal lumen therein adapted to receive a guidewire.

18. The device of claim 15 further comprising a balloon adapted to compress an obstruction in the vessel and further wherein the catheter includes an inflation lumen in operable communication with the balloon.

19. The device of claim 18 wherein the inflation lumen terminates at an opening located near a proximal end of the balloon.

* * * * *